ced by examiner

United States Patent
Krespi et al.

(10) Patent No.: US 7,435,252 B2
(45) Date of Patent: Oct. 14, 2008

(54) CONTROL OF MICROORGANISMS IN THE SINO-NASAL TRACT

(75) Inventors: Yosef Krespi, New York, NY (US); Ashutosh Kacker, New York, NY (US)

(73) Assignee: Valam Corporation, New York, NY (US)

( * ) Notice: Subject to any disclaimer, the term of this patent is extended or adjusted under 35 U.S.C. 154(b) by 249 days.

(21) Appl. No.: 10/929,696

(22) Filed: Aug. 30, 2004

(65) Prior Publication Data

US 2005/0107853 A1 May 19, 2005

Related U.S. Application Data

(60) Provisional application No. 60/511,549, filed on Oct. 15, 2003.

(51) Int. Cl.
*A61N 5/06* (2006.01)
(52) U.S. Cl. .............................. 607/88; 128/898; 607/89
(58) Field of Classification Search ................. 128/898; 607/88–94
See application file for complete search history.

(56) References Cited

U.S. PATENT DOCUMENTS

| | | | | |
|---|---|---|---|---|
| 5,116,311 A * | 5/1992 | Lofstedt | ...................... | 604/516 |
| 5,445,608 A * | 8/1995 | Chen et al. | ...................... | 604/20 |
| 5,611,793 A * | 3/1997 | Wilson et al. | ................... | 606/2 |
| 5,683,436 A * | 11/1997 | Mendes et al. | ................. | 607/88 |
| 6,358,272 B1 * | 3/2002 | Wilden | .......................... | 607/89 |
| 6,533,803 B2 * | 3/2003 | Babaev | ......................... | 607/89 |
| 6,561,808 B2 * | 5/2003 | Neuberger | ................... | 433/215 |
| 6,764,501 B2 * | 7/2004 | Ganz | ............................. | 607/92 |
| 7,107,996 B2 * | 9/2006 | Ganz et al. | .................... | 128/898 |
| 2003/0023284 A1 | 1/2003 | Gartstein et al. | .............. | 607/88 |
| 2003/0153961 A1 * | 8/2003 | Babaev | ........................ | 607/89 |
| 2003/0191459 A1 * | 10/2003 | Ganz et al. | ..................... | 606/15 |
| 2004/0010299 A1 * | 1/2004 | Tolkoff et al. | ................. | 607/88 |
| 2004/0039242 A1 * | 2/2004 | Tolkoff et al. | .................. | 600/9 |
| 2006/0111760 A1 * | 5/2006 | Kemeny et al. | ............... | 607/88 |
| 2006/0293727 A1 | 12/2006 | Spooner et al. | ............... | 607/88 |

* cited by examiner

*Primary Examiner*—Henry M Johnson, III
(74) *Attorney, Agent, or Firm*—K&L Gates LLP

(57) ABSTRACT

Disclosed are methods and apparatus for safe, simple and effective broad-spectrum treatments of chronic rhinosinusitis and other common and less common infections of the sino-nasal tract which may implicate not only a wide range of bacterial species but also fungi and viruses. Electromagnetic radiative energy including visible, and optionally, thermal RF, microwave or other longer wavelengths, is applied to target internal surfaces of the sino-nasal tract to destroy or incapacitate superficial microorganisms without the use of antibiotics. The treatment can be controlled to permit regrowth of healthy microflora. A handheld energy applicator has a light output head receivable into, or engageable with, the treatment subject's nostril which may be provided with extensions to reach the sinuses. Useful embodiments of the invention include pretreatment of target sino-nasal surfaces with a photosensitizing agent such as an oxidizing agent or a complementary stain. For example methylene blue can be used with orange or red light. The combination treatment of photosensitizer and application of visual wavelength energy provides a flexible treatment regimen which enables low concentrations of stains to be employed, minimizing aesthetic problems.

21 Claims, 2 Drawing Sheets

CONTROL OF MICROORGANISMS IN THE SINO-NASAL TRACT

CROSS-REFERENCE TO RELATED APPLICATIONS

This application claims the benefit of Krespi et al. provisional patent application No. 60/511,549 filed Oct. 15, 2003. The subject matter is related to that of Krespi et al. copending Patent Application Publication No. 2006/0047329, entitled "CONTROL OF HALITOSIS-GENERATING AND OTHER MICROORGANISMS IN THE NON-DENTAL UPPER RESPIRATORY TRACT".

STATEMENT REGARDING FEDERALLY SPONSORED RESEARCH OR DEVELOPMENT

Not applicable

BACKGROUND OF THE INVENTION

The present invention relates to methods of treatment and instruments for the control of microorganisms that cause rhinosinusitis and other conditions in the sino-nasal tract and cavities. More particularly the methods and instruments of the invention are useful for the control of chronic or low-level infections of bacteria or other microorganisms causing rhinitis, sinusitis and other chronic conditions. Most of the population suffers rhinitis or sinusitis or both on occasion being usual symptoms of the common cold and influenza. Many people also suffer from persistent chronic sinusitis and/or rhinitis, which may be diagnosed as being attributable to resilient colonies of bacteria that have become established in the nose and/or sinuses. As is well known, the affliction of sinusitis leads to a decrease in productivity and is one of the leading causes of days lost from work due to sickness. Severe and prolonged cases can be seriously debilitating to the unfortunate sufferer.

Some patients undergo surgery to treat chronic sinusitis when antibiotics and other treatment methods have proven ineffective. The objective of conventional sinus surgery is to remove diseased sinus tissue and to open up a pathway for infected material to drain from the sinus cavities. While surgeons can employ sophisticated CT or infrared imaging techniques to map out a patient's sinus pathways there are nevertheless risks of serious complications associated with such sinus surgery arising from the fragility of the sinus walls and their proximity to critical structures such as the brain, eyes, visual cortex and vital vasculature. Accordingly there is a need for an alternative to surgery for treating chronic sinusitis, especially medication-resistant chronic sinusitis.

Common bacteria linked to chronic rhinitis, sinusitis or both, which several conditions are referenced generically herein as "rhinosinusitis", include *Staphylococcus aureus*, alpha-hemolytic streptococci, *Streptococcus pneumoniae*, *Haemophilus influenzae*, coagulase-negative staphylococci, and anaerobes. A complication in devising effective treatments is that other microbes besides bacteria, notably fungi and viruses, may be implicated, including fungi from the aspergillus, candida and penicillium families as well as mycoplasma and Chlamydia, and common cold, influenza and other viruses. It would be desirable to have a simple, safe and effective, broad-spectrum treatment for rhinosinusitis that would control many or most of the infective agents commonly found in the sino-nasal tract.

There exists a large market for nasal rinses and topical application for the control of rhinosinusitis. Many sprays and topical rinses employing topical antibiotic, antifungal, anti-inflammatory agents or mixtures of the foregoing, are readily available. However few treatments available today address the diverse nature of many rhinosinusitis infections which may implicate not only a wide variety of bacterial species but also numbers of fungal and viral species. Many of these species are resistant to conventional remedies.

Notwithstanding the wide range of such remedies that is available, it has been estimated that as many as 20-90 million people in the United States continue to be afflicted with the embarrassment and distress of chronic persistent rhinosinusitis, indicating that available remedies are not fully effective.

Osbakken et al. in U.S. Pat. No. 6,576,224 verify the prevalence of persistent sinusitis and give an extensive description of the anatomy and pathology of chronic sinusitis and of various etiologies and therapies. A detailed discussion of the mechanisms of action and effects of sprays drops and vapors is included. Osbakken et al. propose a sinusitis treatment comprising a unit dosage solution of a pharmaceutical composition comprising one or more of an anti-infective, an anti-inflammatory or a mucolytic agent, together with a surfactant giving the composition a particular surface tension. The composition is intended for application as an aerosolized spray, reportedly minimizing systemic effects and a narrow droplet size range is suggested for efficacy.

Pursuant to the present invention, it can be understood that the ineffectiveness of the treatments may be attributable to multiple factors including: the transient presence of the medications in the vicinity of the microorganisms; the failure of topically applied treatments to penetrate tissue surfaces; to biochemical resistance to the applied treatments; and to the need for continually repeated treatment protocols to which many people will not adhere.

Furthermore, neither systemic nor topical antibiotics are likely to be effective against viral or fungal infections which may be present as predominant or component microorganisms in many infections.

Accordingly, pursuant to the invention, it may be understood that there is a need for rhinosinusitis treatments that are not subject to the foregoing drawbacks.

Electromagnetic energy has been used in various treatments of the sino-nasal tract. For example, lasers have been used for surgery on the nasal septum and turbinates and also on the sinus cavities, principally to reduce tissue volume or to control bleeding. Conditions so treated include hereditary haemorrhagic telangiectasia, also known as Osler-Weber-Rendu syndrome, and vascular lesions.

which
Suitable lasers for such sino-nasal surgery include, with their operational wavelengths shown parenthetically, $CO_2$ lasers (10,600 nm), diode lasers (805/810/940 nm), argon-ion lasers (488/514 nm), KTP lasers (532 nm), Nd:YAG lasers (1,064 nm), and Ho:YAG (2,080 nm) lasers.

Depending on the laser wavelength used, tissue responses, which can be observed by scanning electron microscope, greatly differ with respect to the extent of ablation, coagulation, and carbonization zones. While $CO_2$ lasers can precision cut tissue via ablation with only slight thermal effects on the adjoining tissue, argon-ion-, Nd:YAG-, and diode-lasers tend to cause intense destruction of both the surrounding, superficial respiratory epithelium, and the tissue in the depth of the turbinates or other treated anatomy, resulting from the development of rather large carbonization and coagulation zones. Ho:YAG-light lasers can induce precise vaporization as well as significant superficial coagulation of the tissue.

Some such known laser treatments of the sino-nasal tract are described in the following references:

a) Gerlinger et al. "*KTP-532 Laser-Assisted Endoscopic Nasal Sinus Surgery*". Clin Otolaryngol. 2003 April;28(2): 67-71;
b) Newman et al. "*Applications Of The Diode Laser In Otolaryngology*". Ear Nose Throat J. 2002 December; 81(12): 850-1;
c) Janda et al. "*Comparison Of Laser Induced Effects On Hyperplastic Inferior Nasal Turbinates By Means Of Scanning Electron Microscopy*". Lasers Surg Med. 2002;30(1): 31-9;
d) Kamami Y V, "*Laser-Assisted Outpatient Septoplasty Results On* 120 *Patients*". J Clin Laser Med Surg. 1997;15 (3):123-9; and
e) Levine et al. "*Lasers In Endonasal Surgery*". Otolaryngol Clin North Am. 1997 June;30(3):451-5.

Not surprisingly, none of these disclosures of surgical procedures, which focus on tissue ablation, removal or destruction, remotely suggests a treatment for rhinosinusitis or chronic rhinosinusitis in otherwise healthy and normal subjects. Accordingly, there is a need for less aggressive rhinosinusitis treatments avoiding the drawbacks of medications and which cause little or no damage to the sensitive tissues of the sino-nasal tract.

It is also known that electromagnetic radiation can be employed to destroy different types of bacteria., for example, Phoenix et al. in "*The Phototoxicity Of Plenothiazinium Derivatives Against Escherichia Coli And Staphylococcus Aureus*" FEMS Immunol Med Microbiol. 2003 Oct. 24; 39(1): 17-22 teach that phenothiazinium derivatives like methylene blue and toluidine blue 0 can cause bacterial cell death in both gram negative (*E. Coli*) and gram positive (*Staph aureus*) bacteria by phototoxicity.

However, rhinosinusitis infections commonly comprise a diversity of bacterial and other microorganisms possibly including fungi and/or viruses which factors are not considered by Phoenix et al. Furthermore, Phoenix et al. provide no indication as to whether the responses of the two bacterial species selected for study, one of which is a gastrointestinal species, are likely to be exhibited by all of the diversity of bacterial species that can colonize the sino-nasal tract.

Teichert et al., in "*Treatment of oral candidiasis with methylene blue-mediated photodynamic therapy in an immunodeficient murine model*." Oral Surg Oral Med Oral Pathol Oral Radiol Endod. 2002 February; 93(2): 155-60, described evaluating the efficacy in an immune-compromised murine model of using methylene blue-mediated photodynamic therapy. This is a narrow-focus treatment of a single target fungal organism, oral candidiasis, a pathogen commonly afflicting immune-compromised AIDS patients. The authors reported that methylene blue ("MB") concentrations of 450 and 500 microgram/mL activated with diode laser light at 664 nm using a cylindrical diffuser at 275 J/cm fiber length at 400 mW for 687.5 seconds, were able to "totally eradicate" *Candida albicans* in an immunosuppressed murine model. Teichert et al. professed to be the first to use antimicrobial photodynamic therapy "PDT" in an animal model and to treat oral candiasis by using a methylene blue-mediated photodynamic therapy. Teichert et al. suggests methylene blue-mediated PDT of oral candidiasis as a potential treatment alternative to traditional antifungal drug therapy.

Teichert et al.'s teachings regarding the response of a single infective species in abnormal, immune-compromised mice do not solve the problem of providing a broad-spectrum treatment for a diverse human population most of whom may have normal immunity. Furthermore, Teichert et al.'s treatment is time-consuming having a duration of 687.5 seconds (page 156, right hand column), about 11.5 minutes, and is intended to be applied only to a specific acute care patient group, AIDS patients, rather than to segments of the population that may largely be in moderate to good health.

As an alternative to antibiotic or chemical agents, proposals have been made for the application of radiative energy to the treatment of bodily infections on internal organ surfaces with little attempt to discriminate between potentially hazardous ionizing radiation and relatively safe non-ionizing radiation.

For example, Ganz U.S. Pat. Nos. 6,491,618 and 6,464,625 disclose methods and apparatus employing ionizing radiation, for example, ultraviolet light or x-ray radiation for treating gastrointestinal ailments of a patient including gastritis, gastric ulcer, duodenal ulcer, gastric cancer, gastric lymphoma, ulcerative colitis, or Crohn's disease. Ionizing radiation brings a potential for DNA damage, mutagenicity, teratogenicity and carcinogenicity and is not desirable for the simple, safe treatment objectives of the present invention.

Biel U.S. Pat. No. 6,159,236 discloses a medical device including a tube and expandable member which emits light for photodynamic therapy of internal body surfaces such as the larynx or cheek in order to treat or detect pathologies such as cancer and microbiological pathogens? (what is said about them? nothing?). An integrated array of vertical cavity surface emitting lasers (VCSEL) can provide a light emitting source for photodynamic therapy ("PDT") treatment. Light is transmitted through an expandable member or balloon, which is inflated by air or a fluid, possibly a proteinaceous light-diffusing gel. The expandable member conforms with the surface to be treated. Biel's balloon is undesirable for the objectives of the present invention which also do not relate to cancer detection or treatment.

Other biomedical applications of photothermal energy including external topical application especially for depilation, hair removal, for example, as disclosed in Azar and Shalev U.S. Pat. No. 6,187,001 and Azar U.S. Pat. No. 6,214, 034. Kreindel U.S. Pat. No. 6,702,808 discloses use of light in combination with RF energy for treating hair, vascular lesions and other complex targets on the skin. Hair removal and similar largely cosmetic skin treatments are unrelated to the objectives of the present invention.

The specialist dental field contains proposals for photodynamic treatments of teeth and periodontal areas.

For example, Azar et al. United States Patent Application 20010024777 discloses a toothbrush-like apparatus for self use to effect photothermolysis of oral plaque bacteria sensitized by staining. The apparatus functions to direct light on to at least one tooth. In order to avoid coagulation of blood vessels, light wavelengths near oxyhemoglobin absorption peaks are avoided, e.g. by filtration.

Wilson et al. U.S. Pat. No. 5,611,793 discloses use of laser light in combination with a photosensitizing agent to disinfect or sterilize oral cavity tissues, wounds or lesions. Wilson et al.'s preferred photosensitizers are blue dyes and stains that will absorb red light. Disclosed applications include disinfecting and sterilizing dental tissues, gingival tissues and drilled-out carious lesions prior to filling, destroying cariogenic microbes on a tooth surface, treatment or prevention of chronic periodontitis and inflammatory periodontal diseases; treating oral candidiasis in AIDS patients, immunocompromised patients and patients with denture stomatitis. These dental uses do not teach or suggest nondental applications of the disclosed methods. The application of stain to the teeth may be problematic and unacceptable to patients, discouraging the ordinary worker from adopting Wilson et al.'s methods.

None of the foregoing proposals provides an adequate solution to the problems of providing a safe treatment which is effective for chronic sino-nasal infections and which, preferably is suitable for treating a broad segment of the general population, many of whom may be in good health save for the sino-nasal infection. Nor do known treatments address problems of microorganisms that may be lodged in difficult-to-access locations in the nasal tract.

The foregoing description of background art may include insights, discoveries, understandings or disclosures, or associations together of disclosures, that were not known to the relevant art prior to the present invention but which were provided by the invention. Some such contributions of the invention may have been specifically pointed out herein, whereas other such contributions of the invention will be apparent from their context. Merely because a document may have been cited here, no admission is made that the field of the document, which may be quite different from that of the invention, is analogous to the field or fields of the present invention.

SUMMARY OF THE INVENTION

Pursuant to the invention, it would be desirable to have a simple, safe, broad-spectrum treatment for chronic sino-nasal infections suitable for use by a diversified patient population.

To solve the problem of providing a simple, safe, broad spectrum treatment for chronic sino-nasal infections suitable for use by a diversified patient population, the present invention provides, in one aspect, a method of controlling microorganisms in the sino-nasal tract of a subject, which method comprises applying visible spectrum electromagnetic energy to a microorganism-infected target site in the sino-nasal tract in a dosage effective to control the microorganisms without physiological damage to the tissue, blood vessels, or other anatomy. If desired, the visible spectrum electromagnetic energy can be supplemented with longer wavelength energy, for example heat, radio frequency ("RF"), microwave energy, or equivalents or combinations of the foregoing energy spectra.

The method can be effected by employing a handheld energy applicator instrument having an energy output port receivable in a nostril of the treatment subject. The applicator energy port can be inserted into the subject's nostril prior to the application of photothermal energy. The handheld applicator instrument, which is provided by another aspect of the invention, may comprise a handholdable body accommodating a light source, a light output head comprising the light energy output port and a light transmitting neck supporting the light output head on the handholdable body.

The electromagnetic energy employed can comprise pulses of photothermal energy or diffused diode laser light and is preferably applied without causing tissue ablation, coagulation or carbonization. Some useful embodiments of the invention employ a photosensitizing agent to the target site to sensitize the microorganisms prior to applying the electromagnetic energy. The photosensitizing agent may be a stain which is adsorbed by or adheres to a target microorganism and enhances the absorption of light energy by the organism. Electromagnetic energy having an energy peak overlapping with an absorption peak of the stain can advantageously be used for example orange or red light respectively may be used with a blue or green stain respectively.

If desired, nasal cleansing or irrigation may be employed as a pretreatment prior to the energy treatment of the invention. The pretreatment can comprise one or more of various cleansing or irrigation techniques to remove mucous, superficial colonies of microorganisms and detritus. Such cleansing pretreatment can enhance the efficacy of the radiation treatments or enable the applied radiation to reach deeper seated microorganisms.

The handheld energy applicator instrument can have an energy output port registrable with or receivable into a nostril of the treatment subject so that the energy port can be inserted into the subject's nostril prior to the application of photothermal energy. In cases where the target site is a sinus the method can comprise passing the electromagnetic energy applicator output through a nostril and positioning the applicator energy output to address the target sinus site.

The electromagnetic energy can comprise pulses of photothermal energy having a pulse width of not more than about 200 msec and an interval between pulses of from about 10 to about 2000 msec, along with an energy density at the output of from about 0.1 to about 50 Joule/cm$^2$. The energy application can be performed from about one to about twenty times per month, optionally from about two to about ten times per month, for a period of from about two weeks to about six months. If desired the energy application can be controlled to provide sufficient photothermal energy to effect a microorganism count reduction of at least about 50 percent, optionally about 80 percent without causing physiological damage, pain or discomfort to the patient or subject.

The microorganism population to which the inventive treatments are applied can comprise a heterogenous bacterial population, a fungal population, a viral population, or a mixed population comprising bacteria and fungus or virus or bacteria and fungus and virus.

The treatment methods and apparatus or instruments of the invention provide novel, simple, safe and effective broad spectrum treatments for chronic rhinosinusitis or other low-level infections of the sino-nasal tract. The inventive treatment methods can be quickly and easily carried out in a doctor's or dentist's office, clinic or other medical facility, by a physician or other practitioner, or could be effected by consumers. Systemic or topical drugs are not required and accordingly problems of antibiotic resistance are avoided. Nor is it necessary to employ damaging radiation, such as ionizing radiation which might induce long-term adverse effects.

BRIEF DESCRIPTION OF THE SEVERAL VIEWS OF THE DRAWING

Some embodiments of the invention, and of making and using the invention, as well as the best mode contemplated of carrying out the invention, are described in detail below, by way of example, with reference to the accompanying drawings, in which like reference characters designate like elements throughout the several views, and in which:

FIG. 7 is an anatomical vertical section through a human head illustrating some target treatment sites for the methods of the invention.

DETAILED DESCRIPTION OF THE INVENTION

The following more detailed description of the invention is intended to be read in the light of, and in context with, the preceding summary and background descriptions but without being limited by the preceding descriptions.

In one aspect the invention provides a method of treating low-level infections in the nasal or sinus cavities, the method comprising application to target tissue surfaces in the nasal or sinus cavities, via the nostrils, of sufficient photothermal energy to effect a colony microorganism count reduction of at least about 50 percent. Some useful embodiments of the invention effect a microorganism count reduction of at least about 80 percent, or at least about 90 percent and such a reduction can be effected in a single treatment. The treatments may be repeated, as necessary, to control the microorganism population.

To achieve a desired reduction in microorganism count, the treatment energy can be applied in a dosage which is a multiple of the $LD_{50}$ for a target organism, being the dosage required to kill half the members of a test population of the organism. The dosage can, for example, be a multiple in the range of about 1 to about 3 times the $LD_{50}$, for example about two times the $LD_{50}$ which should provide a reduction of about 90 percent.

The photothermal energy can be produced in any suitable manner, for example by operating a flashlamp to generate a pulsed electromagnetic output comprising both visible light and thermal energy. The energy pulse or pulses produced, or flashes, can be directed to a desired target surface in any suitable manner, for example by reflecting the energy through a window in a housing. The angular divergence of the pulses can be controlled to control the depth of penetration into mucous target tissue, if desired, with wider beams penetrating less deeply, for example by suitable choice of the shape of the reflector and other light guiding surfaces between the source and the target site.

Figure 1:
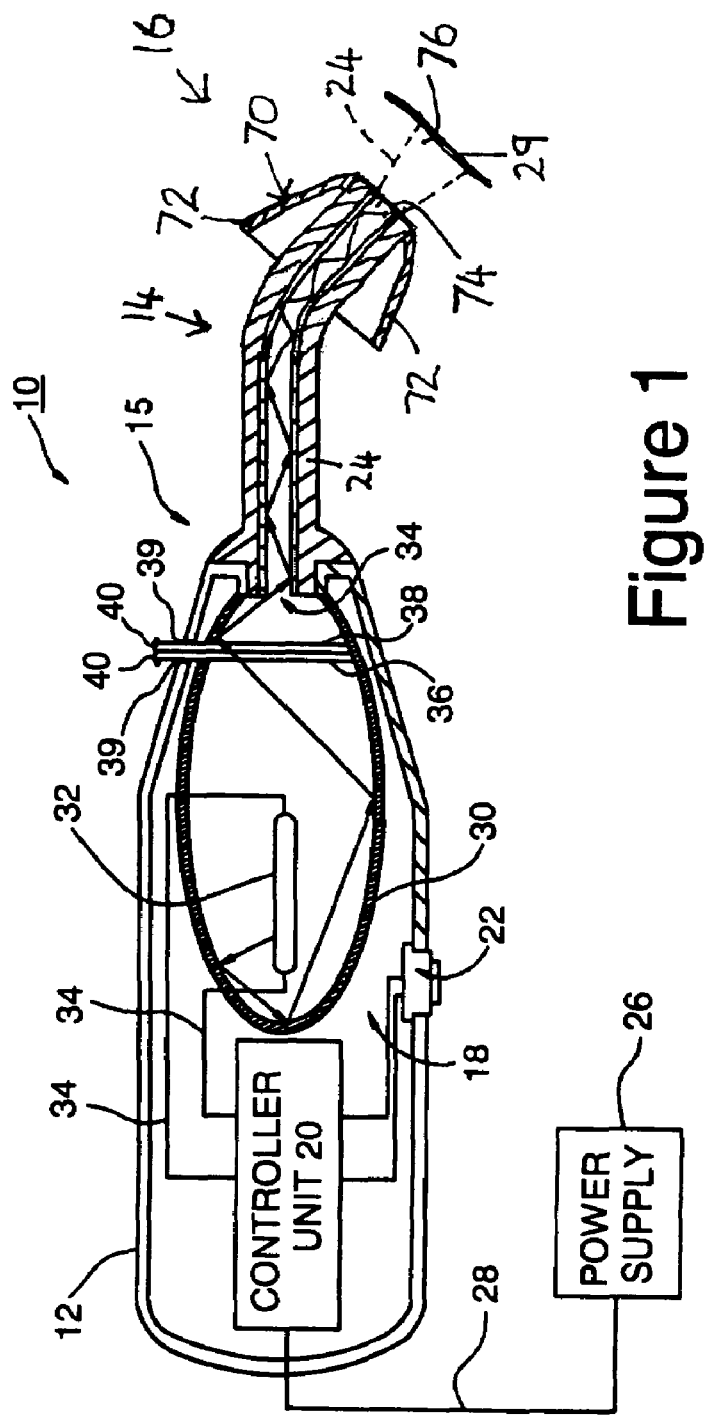
FIG. 1 is a sectional and partially schematic view of a photothermal treatment instrument according to one embodiment of the invention suitable for treating the sino-nasal tract.

Referring to FIG. 1 of the drawings, the photothermal treatment instrument 10 there illustrated is designed to be held and operated in one hand, either the left or the right hand and comprises a partially tapered, generally cylindrical body 12, serving as a handle, from which projects, in the axial direction a neck 14 carrying an output head 16 intended to be inserted into a patient's or user's nostril. As shown, neck 14 can curve or bend away from the axis of cylindrical body 12 to facilitate operation of the instrument while output head 16 is inserted in the nostril.

Figure 3:
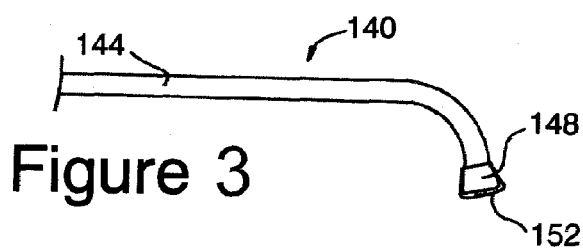
FIG. 3 is a partial view of one embodiment of sinus applicator suitable for use with the photothermal treatment instrument shown in FIG. 1.
Figure 4:
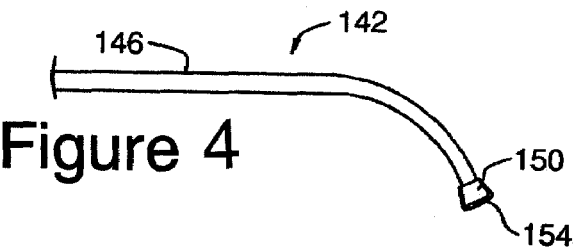
FIG. 4 is a partial view of another embodiment of sinus applicator suitable for use with the photothermal treatment instrument shown in FIG. 4.

With advantage, neck 14 can be releasably attached to body 12 by a joint 15 which can be a push or screw fit, with or without snap engagement or other suitable connection. If desired joint 15 may permit relative rotation between neck 14 and body 12. Neck 14 stably supports light output head 16 on body 12, maintaining light output head 16 in a desired position above body 12 when body 12 is gripped and held in a generally upright position. Thus, light output head 16 can readily be carefully positioned by a physician or other medical practitioner, or self-administrator, to juxtapose light output head 16 to the treatment subject's nostrils. Photothermal treatment instrument 10 can be gripped, manipulated and operated with one hand to inject photothermal energy into the nasal cavity for treating nasal and septal surfaces and, employing extended light guides such as are shown in FIGS. 3 and 4, sinus surfaces.

Cylindrical body 12 houses a light source 18 and controller unit 20 for light source 18 operated by an on-off switch 22. Neck 14 is traversed by a light pipe 24 which guides light from light source 18 to output head 16. As shown, light source 18 is powered from an external power supply 26, via a power cord 28. However, it will 11 be understood that rechargeable or other batteries (not shown) can be housed in body 12, if desired, as either a supplement to or an alternative to external power supply 26.

Body 12 of photothermal treatment instrument 10 can be comfortably gripped in one hand and switch 22 can be operated to activate light source 18 via controller unit 20. Light source 18, when activated, generates light and heat which are transmitted along light guide 24 through neck 14 to be output from output head 16 on to a treatment target site, as will be described in more detail hereinbelow. Body 12, except as may otherwise be apparent herein, can have any suitable cross-section for example, circular, but other cross-sectional shapes, such as oval, rectangular or polygonal that can conveniently be accommodated in a user's hand, may be employed if desired.

As may be understood from FIG. 1, body 12 and its internally accommodated light-generating components can be constructed in a generally similar manner to housing 12 and the light-generating components housed therein disclosed in Azar et al. Pub. No. US 2001/0024777, particularly in FIG. 3 and at paragraphs [0075] to [0080] the entire disclosure of which patent publication is hereby incorporated herein by reference thereto. However, in the currently described embodiments of the present invention, the energy delivered, the light delivery system and the target sites are, or can be, quite different from Azar's intended destruction of sensitized plaque bacteria on the teeth.

Incoherent light source 18 in body 12 can include a lamp reflector 30 and a lamp 32 disposed within reflector 30. Lamp 32 is electrically connected to controller unit 20 via leads 34 and is powered from power supply 26 in response to actuation of switch 22 under the control of controller unit 20. If desired, lamp 32, and optionally also, reflector 30 can be user removable and replaceable in body 12 to enable the user to replace lamp 32 with a lamp having different energy output characteristics during a treatment procedure. For this purpose, body 12 may have an access opening and cover therefor (neither one shown).

Lamp reflector 30 can have any suitable shape to collect light from lamp 32 and reflect the collected light into light pipe 24, via a proximal opening 34. The lamp shape may, for example, be ellipsoidal, quasi-ellipsoidal, parabolic, quasi-parabolic, spherical, quasi spherical or the like.

If desired, one or more filters, such as are shown at 36 and 38, can be provided in the light path between lamp 32 and proximal opening 34 to limit the spectrum of the output light. Preferably, filters 36, 38 are selectively removable from body 12, for example through slots 39 by grasping tabs 40 which project externally of body 12, to enable a user to select desired filtration characteristics. Filters 36, 38 and any other optical components in the light path from lamp 32 to the target site are preferably heat-transmissive to permit heat from lamp 32 to be applied to the target site along with light, duly filtered, if desired. By inserting or removing one or more of filters 34, 36, a user may vary the filtration, for example, between zero filtration and a high degree of filtration provided by a low bandpass and a high bandpass filter with adjacent cutoff frequencies which provide an output with a particularly narrow waveband, if desired. Some useful frequency ranges such as blue, blue-green or orange with or without limited ultraviolet, are described hereinbelow. Suitable filters 34 and/or 36, or possibly even three filters, that can be employed to provide desired outputs, as described herein, will be apparent to those skilled in the art. If desired, without limitation, filters 34, 36 may comprise: a single blue filter, for example a filter having a transmission spectrum wherein at least about 90 percent of the energy lies between about 400 to about 500 nm; a single blue-green filter, for example a filter having a transmission spectrum wherein at least about 90 percent of the energy lies between about 400 to about 600 nm; an orange filter transmitting at least about 70 percent of the incident infrared energy, which may optionally transmit at least about 90 percent of the energy at wavelengths of about 600 nm and longer; or an ultraviolet filter transmitting no more than 10 percent of incident UVC, and optionally, no more than about 40 percent of incident UVA and UVB.

Alternatively, the ultraviolet filter may transmit no more than about 10 percent of incident UVA, UVB and UVC radiation. In other embodiments of the invention, filters, 34, 36 can comprise an ultraviolet filter as described and one of the blue, blue-green or orange filters, as described.

Lamp 32 can be any suitable lamp providing an incoherent broadband light output with an appropriate energy-versus-wavelength output spectrum for the purposes of this invention. Lamp 32 may for example be an arc discharge lamp, a flash lamp, such as a xenon or quartz xenon flash lamp, or other suitable lamp and may have a peak energy output around 500 nm or at other suitable wavelength. Such a lamp will generally deliver heat energy as well as light. For treatments limited to blue-rich light, other light sources may be employed for lamp 32, including sources delivering little or no heat energy and having peak energy outputs at shorter wavelengths.

As indicated above, photothermal treatment instrument 10 can be designed for lamp 32 to be readily changed by a user. In this case, photothermal treatment instrument 10 can include multiple lamps 32 having different output characteristics enabling the user to vary the energy output during a treatment procedure. The outputs can be comparable with or equivalents of the outputs obtainable with filters 34, 36 and may be suitably modified with filters, if desired. It will be understood that a suitable filter or filters can be selected for use with a particular lamp and changed when the lamp is changed, if desired.

Lamp 32, when utilized in photothermal treatment instrument 10 can be such as to provide an output capable of photothermolysis of stained or unstained bacteria, and other microorganisms resident on or populating mucous tissues in desired target areas, preferably without significant tissue damage.

Controller unit 20 includes suitable circuitry to operate flash lamp 32 with desired pulse characteristics, as will be described. The circuitry (not shown) can include a triggering unit, a capacitor unit and electronic timing circuitry for timing the flash frequency.

Neck 14 is preferably rather short and curved or angled, along its length, about an axis transverse to its length, as illustrated, so that light output head 16 can be partially inserted in the nasal cavity with body 12 conveniently downwardly disposed. Alternatively neck 14 can be rectilinear. The length of neck 14 is preferably kept to a minimum effective for convenient and ergonomic operation. Light pipe 24 can be a reflectively lined tubular passage, fiber optic or other suitable light-conveyance device and neck 14 can be formed of a suitable structural material, preferably a heat- and light-insulating material.

Light output head 16 comprises a funnel- or frustoconical-shaped nozzle 70 which is designed to be a close fit within a subject's nostril and has outer flanks 72 extending around light pipe 24. Desirably, flanks 72 are configured and otherwise designed to comfortably seat against the subject's nostril. The external configuration of nozzle 70 can be similar to what is known for inhalers used to administer sprays, mists and the like. Reflectively lined light pipe 24 can be of constant cross-section along its length. Alternatively, in one useful embodiment of the invention, light pipe 24 can have a distally increasing cross-section (not shown) toward an outlet port 74 to provide a flared or divergent output beam 76, spreading the photothermal energy for good coverage of the irregular configuration of the surfaces of the lower and upper nasal cavities. However, a cylindrical or other appropriate shape of the internal surfaces of light pipe 24 may be useful, in some cases to provide a pencil beam for more localized treatment of the nasal cavity or to better treat the upper nasal cavity. Desirably, nozzle 70 has a circular cross-section, although other suitable shapes may be employed, and is provided in a range of sizes to fit different nasal anatomies, including e.g. smaller for children and larger for adults, in a manner known generally to the art. Depending upon its size, nozzle 70 can have an outlet 74 with a diameter in the range of from about 1 to about 10 mm, desirably from about 3 to about 7 mm.

Nozzle 70 can be detachably attached to neck 14 enabling different sizes and possibly shapes of nozzle 70 to be used interchangeably. Also, disposable nozzles 70 can be utilized, permitting a new, sterilized nozzle to be used for each treatment. Such a disposable nozzle 70 may have a centrally depending, internally reflective tubular portion extending into light pipe 24, if desired, for hygienic purposes. Another alternative is for neck 14 to be detachably attached to body 12 of photothermal treatment instrument 10 enabling alternative applicators such as the sinus applicators shown in FIGS. 3 and 4 to be utilized in place of neck 14 and nozzle 70. Optionally, neck 14 can be rotatable on body 12.

It will be appreciated that output port 74 and the other components of photothermal treatment instrument 10 can have any structure which will provide suitable energy pattern areas on a desired target site with sufficient energy intensity to provide effective microorganism control.

In many desirable embodiments, but not necessarily all embodiments, the energy output from lamp 32 travels entirely through air or breath from filter 34 or 36, or from lamp 32 if no filter is employed, to target surfaces or materials within the subject's nasal or sinus cavities.

For application of radiant heat energy or, preferably heat and light energy, to the target site, lamp 32 can be selected to be a thermal emitter having a heat transmissive glass, e.g. quartz glass, borosilicate glass or other suitable enclosure or bulb. To avoid undue attenuation of the heat energy before it reaches the target site, photothermal treatment instrument 10 can be formed with a clear path from lamp 32 to the target site which is free of heat attenuating elements that are strong infrared absorbers, for example, infrared-blocking glass lenses or filters. For example, the light path through photothermal treatment instrument 10 from lamp 32 to the target site may be entirely through air, or other gas or vacuum, and through heat and light transmitting members, desirably members formed of quartz glass or an equivalent. Thus, for delivery of heat as well as light to the target 29, filters 36, 38, or other radiation transmissive elements between the energy source and the target, if employed, may be formed of a suitable glass such as an orange or red glass with good infrared transmissivity, e.g. quartz glass or a more exotic glass such as an infrared transmitting chalcogenide or chalcohalide glass, as is known to those skilled in the art.

Materials. Photothermal treatment instrument 10 can be manufactured of any suitable materials as will be apparent to those skilled in the art for example, moldable thermoplastic or thermosetting polymers and/or resins and may be of rigid construction. However, the invention also includes embodiments where neck 14 or light output head 16, or both, are flexible and, optionally, resilient. For example, neck 14 could be flexible to facilitate orientation or location of light output head 16. Another option is neck 14 or nozzle 70, or both, to be deformable, permitting the user to change the orientation of nozzle 70 with respect to body 12 or to better conform nozzle 70 to the subject's anatomy or possibly, to modify the shape of the output photothermal beam.

Disposability. As described above, output head 16 and also neck 14 can be removably attachable to body 12 which houses light source 18 and associated electrical equipment. By making output head 16 and/or neck 14 of economical construction, for example plastic moldings, they can be rendered disposable. Thus a new head 16, optionally with a new neck 14, can be employed for each new patient, or each new treatment, avoiding need for sterilization of a component for reuse. However, if desired, neck 14 and optionally also output head 16 could be sterilized and reused for multiple treatments. Where photothermal treatment instrument 10 is dedicated to a single patient or consumer, sterilization may not be necessary.

Figure 2:
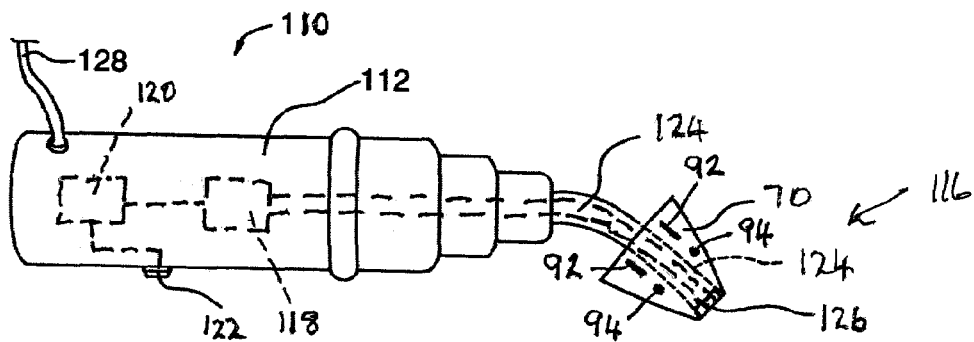
FIG. 2 is a side elevational view of a photic treatment instrument according to another embodiment of the invention which is also suitable for treating the sino-nasal tract.

The embodiment of photic treatment instrument 110 for nasal applications as shown in FIG. 2 is generally similar to the FIG. 1 embodiment but has a more compact body 112 for convenience bearing a light output head 116 similar to light output head 16. Photic treatment instrument 110 can be usefully embodied in an end user product with lower maximum photothermal energy output, for example a low cost unit for personal use. Instrument 110 is activated by a control button 122 and power is supplied through a power line 128. Instrument 110 can employ a scaled down version of the photothermal energy output device 18 of FIG. 1, if desired. Alternatively, either instrument 10 or 110 may be equipped with a diode laser 118 controlled by a suitable controller 120 in which case light pipe 24 can be replaced by a fiber optic light connection 124 and light output head 116 can employ a suitable diffuser 126 which preferably projects the light forwardly and spreads the laser beam over a wider area, for example with a beam angle of between about 10° and about 170° optionally between about 30° and about 120°.

Referring now to FIGS. 3 and 4, sinus applicators 140, 142 can be provided to access a patients' sinus cavities via their nostrils and to output photothermal energy into one or more target sinus cavities. Sinus applicators 140, 142 have relatively thin elongated and curved shafts 144, 146 respectively, to extend into and through the nasal cavity and terminate in relatively small nozzles 148, 150 with small outlets 152, 154, respectively, intended to direct light transversely to the respective shaft 144 or 146 and into a sinus cavity to be treated when the sinus applicator is suitably positioned. Sinus applicators 140, 142 are also provided with internal light pipes (not shown) which may be flared, if desired, at their distal ends to provide a flared light output beam.

In another alternative embodiment, electrical rather than photothermal energy is transmitted from handheld body 12 through neck 14 to light output head 16 where the energy is converted to light, simplifying the construction of neck 14. For this purpose, a suitable, relatively smaller embodiment of lamp 32, e.g. a bulb-shaped embodiment, can be provided in light output head 16, within or adjacent to nozzle 70 displacing most or all of light pipe 24. Such a smaller lamp 32 can be supplied with electricity via conductors such as 34, extending through neck 14 from controller unit 20.

Chemical Sensitization. Some, but not all, preferred embodiments of the invention employ a chemical sensitization agent as a pre-treatment to sensitize target microorganisms to the effects of the applied photothermal radiation and enhance microbial kill rates. Some suitable sensitizers include dyes such as methylene blue and oxygen gels containing, for example peroxide. Other suitable agents are described in more detail hereinbelow.

Figure 6:
FIG. 6 is a plan view of another embodiment of sinus swab suitable for applying a photosensitizer to the sinus cavities.
Figure 5:
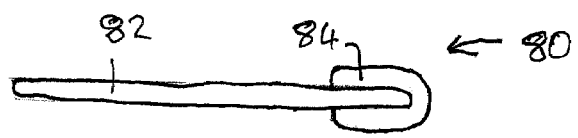
FIG. 5 is a plan view of one embodiment of nasal swab suitable for applying a photosensitizer to the nasal cavities.

Such sensitizers are conveniently applied in liquid form employing applicators such as are shown in FIGS. 5 and 6. Nasal swab 80 shown in FIG. 5 comprises an elongated support 82 to one end of which is secured a sterile pad 84 of cotton, foam or other suitable absorbent material. Nasal swab 80 may for example be a calcium alginate fiber haemostatic swab. Sinus swab 86 is similar to nasal swab 80, with the difference of having an elongated support 88 which is curved or angled at one end. Also pad 90 may be a little smaller than pad 86, to better adapt sinus swab 86 to apply fluid to the sinus or sinus passages. If desired support 88 of sinus swab 86 can be flexible to facilitate accessing the sinuses with sensitizer fluid-impregnated pad 90. In use, pad 86 or 90 is dipped in a source of suitable topical pre-treatment fluid, for example a sensitizer, while manually gripped by the respective support 82 or 88, is manually inserted through the nostril and contacted with a desired target surface to apply the fluid to the target surface.

Photosensitizing Agents

As described in more detail hereinbelow, photosensitizing agents such as stains, liquid compositions colored with dyes or pigments, may be employed to enhance the treatment process. Desirable aspects of the invention employ a combination of stain and energy dosage which is effective, of convenient duration and aesthetic. A benefit of the invention is that, unlike dental applications where whiteness of the teeth may be paramount to the subject, the sino-nasal surfaces to which the treatments of the invention are applied in most cases conceal, or substantially conceal applied stains. Biocompatible photosensitizing stains showing strong absorbance of one or more peak wavelengths output by the light source or other source of electromagnetic radiation are particularly useful in enhancing the efficacy of the energy treatments or in rendering lethal energy dosages that might otherwise be innocuous. However, excess and displaced stain may be problematic and unaesthetic if the stain exhibits itself to the subject after treatment, for example, after blowing their nose.

To control such problems while benefiting from the lethality and efficacy that use of a suitable stain can bring, the stain can be employed in relatively low concentrations, for example a concentration of less than 1%, referring to methylene blue. In practice, concentrations of less than 0.1%., for example 0.08% or lower, are desirable to avoid aesthetic problems over an extended time period. In general, again referring to methylene blue, some useful microorganism lethality can be obtained with concentrations of 0.01% or greater, although extended energy exposures may be necessary at such concentrations. Some particularly useful embodiments of the invention employ concentrations of methylene blue in the range of from about 0.02 to about 0.08%. Concentrations of methylene blue in the range of from about 0.03 to about 0.06% are also believed to be particularly effective. It will be appreciated that other stains may employ different concentrations according to their efficacy as known or as determined by routine experimentation.

In one embodiment, the invention employs a low or the minimal effective dosage of stain which is sufficient to obtain a useful or desired reduction of harmful microbes. Optionally, the dosage may be selected to leave a residual population, perhaps 10 or 20% to promote the proliferation of healthy microflora.

Such modest stain concentrations may be relatively aesthetic, providing only modest, or short-lasting coloration, yet have little, if any lethal effect when used alone. However they can provide a surprising enhancement of the efficacy of the energy treatment, reducing the effective dosage and thence the risks of physiological damage or the treatment duration.

Some specific photosensitizers which may be used in practicing the invention, as alternatives to methylene blue, include, for example, photosensitizers selected from the group consisting of stains, dyes, pigments, arianor steel blue, toluidine blue, tryptan blue, crystal violet, azure blue cert, azure B chloride, azure 2, azure A chloride, azure B tetrafluoroborate, thionin, azure A eosinate, azure B eosinate, azure mix sicc., azure II eosinate, haematoporphyrin HCl, haematoporphyrin ester, aluminum disulfonated phthalocyanine and chlorins. Other photosensitizing agents may also be used, as will be apparent to those skilled in the art, including, for example, suitable biocompatible oxidizing agents such as dilute hydrogen peroxide or other biocompatible oxidizing agents.

Desirably, photosensitisers such as the haematoporphyrins which are not well taken up by Gram negative organisms, if selected for use, are employed in treating microorganism colonies that are rich in Gram positive bacteria. Various dyes such, for example, as aluminum disulfated phthalocyanine, toluidine blue, azure B chloride or methylene blue can, without limitation, be employed for treating Gram negative organisms. In embodiments of the invention practiced utilizing an He Ne laser desirably, tryptan blue or crystal violet are not employed.

Some useful combinations of photosensitizer agent and light wavelength include toluidine blue irradiated with optical or photothermal energy including a peak or peaks at or near a wavelength of about 630 nm and aluminum disulfonated phthalocyanine irradiated with optical or photothermal energy including a peak or peaks at or near a wavelength of about 660 nm.

Kits. If desired, embodiments of photothermal treatment instrument 10 can be supplied as kits comprising one or both of photothermal treatment instrument 10 and 110 and, optionally, one or more other similar photothermal treatment instruments adapted for treatment of other sites or for providing different treatments pursuant to the invention herein. Such kits can also include one or more replacement or alternative light output heads 16 together with a suitable selection of nozzles 70, sinus applicators 140 and 142 and optionally one or more interchangeable filters 34, 36. For example, one embodiment of useful rhinosinusitis kit can comprise a photothermal treatment instrument 10 or 110 together with at least two nozzles 70, or nozzle-light pipe combinations, and one each of sinus applicators 140 and 142. Preferably a multiplicity of disposable nozzles 70 is included, for example a stock of between about 4 and 100 nozzles 70. If desired one or more swabs such as nasal swab 80 and sinus swab 86 is included, for example a stock of from about 4 to about 100 of each swab. In addition, a stock of suitable photosensitizer agent can be included, for example from about 0.5 to about 100 ml of methylene blue or other suitable agent as described herein. Bulk supply kits can be supplied to professionals such as physicians and medical facilities whereas individual kits comprising only one or two items of each or a selection of the foregoing components can be suitable for marketing to consumers.

Energy sources. A variety of energy sources can be employed for the photothermal treatment instruments of the invention including for example pulsed light, pulsed heat and light, and continuous or pulsed LED or laser sources. If a laser is utilized, it is preferably a low intensity or relatively low intensity laser provided with a diffuser to spread the output radiation. The energy system desirably outputs energy over a target area or in a target pattern which is neither a thin pencil, which would make coverage of the target difficult, nor an area so wide as to render the received radiation too weak to be effective.

One embodiment of the invention (not illustrated) employs, as an alternative to the type of light source employed by Azar et al. and described hereinabove, an electromagnetic energy source such as the incoherent pulsed light sources disclosed in Eckhouse et al. U.S. Pat. No. 6,514,243, the entire disclosure of which is hereby incorporated herein by reference thereto. Eckhouse et al. employ, for removal of hair from the skin by means of electromagnetic follicle destruction, a gas filled flashlamp, such as a xenon-filled linear flashlamp ILC Technologies model no. L5568. Xenon-filled flashlamps having suitable characteristics can be employed as photothermal energy sources in the present invention, for example (?see brochure).

Character of Energy Output. Depending upon the nature of the organism or organisms to be controlled, the applied energy delivered from output head 16 to the target site can be either heat energy alone or light energy alone but is preferably a mix of heat and light energy. The energy should be applied in a quantity and at a wavelength effective to obtain a desired reduction of the colony microorganism or microorganisms to be controlled. In one embodiment of the invention about 80 percent of the applied energy reaching the target site can be heat and about 20 percent can be light. These quantities can of course vary substantially for example within the ranges of from about 60 to about 90 percent heat and about 10 to about 40 percent light.

Preferably the light energy employed includes visible wavelengths and optionally it may include a minor proportion of ultraviolet light in the wavelengths for UVA or UVB or both. However it is usually desirable to avoid UVC wavelengths which may induce DNA or other damage to human tissue. Another embodiment of the invention substantially excludes all wavelengths of ultraviolet, or has minimal or modest ultraviolet, for treatments where the potential carcinogenicity, or other potentially harmful effects of ultraviolet light are unacceptable.

As described elsewhere herein, particularly in relation to filters 34, 36 the invention can employ pulses of photothermal energy rich in blue light, having for example at least 70 percent or even at least 90 percent of the pulse energy in visible wavebands is contained in a relatively narrow blue waveband of from about 400 to 500 nm or a blue-green waveband of from about 400 to about 600 nm.

As described above, utilization of Azar et al.'s apparatus for destroying sensitized, e.g. selectively stained, oral bacteria within dental plaque, is preferably effected, according to Azar, by employing energy filtered to exclude the absorption peaks of oxyhemoglobin at wavelengths of 418 nm, 542 nm and 577 nm and neighboring wavelengths, to avoid undesired coagulation of blood vessels (paragraph [0066]). Blood vessel coagulation can be understood to be a risk of Azar's procedure, intended for consumers, which employs staining in the dental area where gingivitis and associated bleeding, is common. In contrast, the present invention can, in some embodiments, include energy at the oxyhemoglobin absorption wavelengths to be excluded by Azar et al. Indeed, as described hereinabove, photothermal energy rich in polychromatic blue light in the waveband of 400-500 nm or polychromatic blue-green light in the waveband of 400-600 nm can be particularly useful for the treatment of bacteria colonies resident on or in nondental upper respiratory mucous tissues. where. It is contemplated that coagulation of blood vessels will not usually occur, or will not be a problem, with the treatments of the invention described herein.

While the invention is not limited by any particular theory, it is contemplated that light may often be effective to reduce superficial colonies of microorganisms at the target, i.e. microorganisms that are essentially on the surface of the target. Light may also incapacitate microorganisms up to a depth of about 1 to about 1.5 mm. However, light may not adequately penetrate deeper layers of tissue. Accordingly employment of near infrared or longer wavelength heat energy that can penetrate the superficial layers and reduce microorganisms in lower layers of the tissue is contemplated as an advantageous but optional, feature of the present invention. Preferably, such heat energy is applied simultaneously with the light energy and from a common source.

Pursuant to one embodiment of the invention, a microorganism control treatment can comprise an application of photothermal energy, e.g. one or two pulses, rich in blue light to control superficial microorganisms and a separate application of photothermal energy, e.g. one or two pulses, of orange or other longer frequency radiation to control deeper microorganisms.

By employing light energy in conjunction with mild heat energy, many microorganisms can be effectively destroyed photochemically, possibly avoiding the need to use more intense heat to raise the tissue temperature to the coagulation temperature of the microorganism. Such an embodiment of the invention can be employed where a patient has particularly sensitive, or previously damaged tissue, or there is a particular concern to avoid tissue damage. Furthermore, mild heating can increase the local blood flow, facilitating the elimination of bacteria or other microorganisms.

The applied energy can be selected to include wavelengths, in addition to visible light wavelengths, that both elevate the temperature of the target to cause thermal damage to colonies of microorganisms resident at the target and also to accelerate destructive photochemical reactions. The energy can be selected to include wavelengths absorbed by the mucous tissue at the target which is impacted by the applied radiation.

Pursuant to the invention, it is desirable to destroy microorganisms resident on or in the target tissue without damage to, or with only minimal damage to, the tissue itself and without causing the patient pain, soreness or other undesired reaction. To this end in one embodiment of the invention the tissue temperature can be raised to a temperature in the range of from about 50° C. to about 70° C., preferably to about 60° C., for example in the range of from about 57° C. to about 63° C. The temperature of the target tissue can be determined in known manner or by employing a thermosensor (not shown) carried by the photothermal treatment instrument 10 and operated during, or preferably, promptly after application of a photothermal treatment.

If desired the instrument can be calibrated by performing a number of treatments with different durations, intensities and targets and detecting the resultant target temperatures. Using this information, settings and protocols can be provided for future procedures that will yield appropriate target temperatures with reasonable confidence, without the need for real time temperature determinations.

The period of elevated temperature is preferably of the order of about 1 minute for example from about 5 seconds to 5 minutes or in the range of from about 20 seconds to 2 minutes, or from about 40 to about 80 seconds. A desired period of elevated temperature may be achieved by application of one or more energy pulses, up to no more than about ten pulses within the period, each pulse being of brief duration, as described herein, and each being followed by a quiescent interval providing for tissue relaxation.

One example of effective heat energy is the infrared energy of a $CO_2$ laser at a wavelength of about 10,540 nm which wavelength is very efficiently absorbed by water and may be employed, preferably in conjunction with other frequencies, as described herein. If laser energy is utilized for the practice of the invention, it can be diffused, using a diffuser to spread the energy over a desired tissue area and avoid tissue damage, and, preferably is also, supplemented with other frequencies.

Pulsed or continuous energy. Some other useful embodiments of the invention employ pulsed rather than continuous energy sources to provide high peak power and efficient photochemical activation of harmful chemical species in the microorganisms or in treatment materials such as oxygen gels, if the latter are employed. Other embodiments can employ continuous energy sources, if desired.

In the application of heat, use of a pulsed source can be helpful as pulsing allows for thermal relaxation of the tissue in the troughs between peaks preventing localized overheating of and damage to tissue.

Useful pulsed radiation for practicing the invention can have a pulse width of not more than about 200 msec, for example from about 10 to about 100 msec. In one useful embodiment of the invention the pulse width is about 25-35 msec. If multiple pulses are applied at one time, there is desirably a delay, providing a tissue relaxation interval between pulses of the order of from about 10 to about 2000 msec, desirably from about 20 to about 100 msec, for example about 40 or 50 msec, to permit tissue relaxation and prevent tissue damage.

The pulse energy delivered to the target sites should be sufficient to be effective in controlling microorganisms without causing tissue damage such as to be normally perceived by the patient or that would be harmful to the patient. For example, energies of from about 0.1 to about 5 $J/cm^2$, preferably from about 0.5 to about 3.0 $J/cm^2$ may be employed.

Typically, individual light flashes can have durations in the range of about 0.1 to about 10 msec and irradiates internal sino-nasal surfaces with incoherent light. The light can be band-limited by suitable filtration, if desired and longer duration flashes up to about 2000 msec may be employed, if desired. The output energy density at outlet port 73, or other suitable energy output port, can be from about 0.1 to about 50 $Joule/cm^2$. Some embodiments of the invention can employ energy densities of from about 3 to about 20 $joules/cm^2$, for example from about 7 to about 12 $joules/cm^2$. Other useful embodiments of the invention can employ energies of from about 0.1 to about 5 $J/cm^2$, preferably from about 0.5 to about 3.0 $J/cm^2$. The peak energy waveband can be selected to be at, to include, or to overlap the bacterial stain sensitization peaks, for good efficiency.

The duration and energy density are desirably controlled to heat stained bacteria and other microorganisms to a destruction temperature such as their temperature of coagulation, while avoiding tissue or other physiological damage. Using energy densities within this range, even a single flash can, in many cases, effectively cause photothermal heating and coagulation of selectively stained sino-nasal bacteria.

Optionally photothermal treatment instrument 10 may have settable controls to provide different predetermined dosages, which controls may be labeled. For example, a duration controller may be provided for selecting the pulse duration or pulse width e.g. from about 10 to about 50 msec, and a pulse number selector may select the number of pulses output for a single actuation of photothermal treatment instrument 10, for example from 1-10 pulses, at a predetermined relaxation interval, for example of from about 10 to about 100 msec.

One useful embodiment of energy application protocol employs a xenon flashlight and an orange filter, transmission about 600-700 nm, with two photothermal energy pulses of about 35 msec, with a 50 msec interval, at an energy density of about 2.5 J/cm$^2$. An energy waveband output through an orange filter is strongly absorbed by methylene blue-stained organisms. Different filters may be used with different stains to provide good absorption, for example a green filter may be used with a pink stain.

Another useful embodiment employs light at 760 nm from a laser diode at an energy of 50 milliwatts/cm2 for a duration of 30 seconds.

If employed, the heat energy may be provided by any suitable source, for example infrared radiation, convection, conduction or in situ induction by RF or microwave energy or the like. If desired, RF or microwave energy may be applied to obtain useful therapeutic results in conjunction with light and/or a heat source. It will be understood that RF or microwave or equivalent energy fluxes can be employed to provide useful microorganism control effects by mechanisms other than local heating, for example by electroporation (cell membrane pore formation) or cell membrane rupture. Some, but not all, useful embodiments of the invention employ light, optionally in combination with another energy source.

The electromagnetic energy can be applied in any suitable wavelength mode, waveband mode or combination of wavelength and/or waveband modes which is or are effective to provide control of one or more target microorganism species without causing unacceptable pain, trauma or other side effects. A suitable source or combination of sources can be provided to generate or introduce the desired energy or energy mix in situ.

For example, any combination of two or more of light energy, heat energy, radio frequency ("RF") and microwave energy may be employed in the inventive treatments, if desired. Some useful treatment embodiments of the invention apply light energy together with heat energy and may optionally also apply RF or microwave energy. In alternative embodiments, a light energy mode is employed together with a heat energy mode, a microwave or RF mode or with a heat energy mode and a microwave or RF mode. Useful embodiments include heat energy modes wherein the heat energy is generated by RF or microwave radiation. Alternatively, the heat energy mode may comprise infrared radiation.

The invention includes embodiments wherein two or more energy modes are applied essentially simultaneously. By "essentially simultaneously" is meant that the two energy modes are applied simultaneously, or are applied in rapid succession, one after the other, such that significant cooling of the target does not occur between the first and second applications of energy.

Each energy mode source or applicator can be any suitable device as known to those skilled in the art. Combination devices and methods such as disclosed in Kreindel U.S. Pat. No. 6,702,808, the entire disclosure of which is hereby incorporated herein by this specific reference thereto, can also be employed. The invention includes novel uses of such devices and novel combinations and modifications of such devices adapting or combining them for the purposes of the invention, as will be apparent to those skilled in the art in light of the disclosure herein.

By way of example, the energy applicator device can include a light source to emit optical energy, one or more electrode pairs 92 for generation of RF energy and/or microwave elements 94 for generation of microwave energy. Optionally, the light source may also provide an effective intensity of heat energy. Pulsed RF energy applied by the electrodes can be applied to the target tissue either directly or through a conductive substance.

Usefully, the frequency of the RF energy can be in a range of from about 300 kHz to about 100 MHz, the output power can be from about 5 to about 200 W, pulse duration from about 1 to about 500 msec and the pulse rate can be from about 0.1 to about 10 pulse per second. Frequencies, or frequency ranges, in spectral locations assigned by governmental entities for industrial, scientific and/or medical purposes are particularly useful, including for example in the United States, FCC-assigned frequencies of about 13.56 MHz, 27.12 MHz and 40.68 MHz.

The optical energy employed with such an RF energy mode can have an intensity of from about 5 to about 100 Joules/cm2 and a pulse duration of from about 1 to 200 msec. The individual or combined energy dosages desirably are selected to avoid long-term physiological damage or unacceptable discomfort pain or other immediate adverse effects.

Visible light, if employed, may have a single wavelength, multiple wavelengths or a waveband and this or these are preferably selected according to the absorbency of the target organism or organisms, and are typically in the range of 500 to 1200 nm. Other energy modes, if employed, may also have a single wavelength, multiple wavelengths or a waveband or wavebands.

Microwave energy for use in the invention can be of any suitable frequency for example in a range of from about 100 MHz to about 50,000 MHz, the output power can be from about 0.01 to about 10 watts/ml of target volume, optionally from about 0.1 to about 2 watts/ml. Frequencies, or frequency ranges, in spectral locations assigned by governmental entities for industrial, scientific and/or medical purposes are particularly useful, including for example in the United States, FCC-assigned frequencies of about 915 MHz, 2,450 MHz, 5,800 MHz and 24,125 MHz.

Selection of a suitable energy mode or mix of energy modes to provide an effective treatment can be made on the basis of the teachings herein with the assistance of knowledge in the art, if desired. For example, useful guidance regarding antimicrobial energy treatments may be found, inter alia, in the food processing arts, for example in disclosures such as the USFDA Center for Food Safety and Applied Nutrition publication "Kinetics of Microbial Inactivation for Alternative Food Processing Technologies", dated Jun. 2, 2000. Of particular interest is the section headed "Microwave and Radio Frequency Processing" and section 3.3 thereof.

RF and microwave energy fluxes are useful for their rapid and uniform effect and ability to penetrate subepithelially to reach microorganisms harbored in tissue crevices, folds, pockets and the like and organisms overlaid with other material, e.g. coatings or other microorganisms. Suitable guides and screens or other protective structure can be provided to introduce the desired energy flux to the target area while protecting the subject anatomy from incidental harm. The intensity and duration and other characteristics of the energy flux can be selected with these objectives in mind, without undue experimentation, and pursuant to the principles described in more detail herein for application of light or heat.

The invention includes treatment methods employing a mix of energy modes selected to provide comprehensive therapy at a target site by killing or otherwise controlling a broad spectrum of undesired microorganisms resident at the target site wherein effective energy dosages are applied so as to reach not only superficially resident microorganisms, but also deeper layers or volumes of the target site that are believed to harbor undesired microorganisms. When safely introduced to the target site, RF or microwave energy fluxes are believed useful to this end for their relatively uniform or distributed effects in solid materials especially high water solids such as tissue or other anatomical structures.

Colony count. In one embodiment of the invention, the photothermal treatment is applied in a manner such as to obtain a desired reduction of colony count of a target microorganism or microorganisms, for example a broad spectrum bacterial infection or infection by an antibiotic-resistant strain or strains of bacteria. Pursuant to this embodiment of the invention, parameters such as the intensity and spectrum of the applied energy and the duration of treatment are controlled to obtain a desired colony count reduction of the target microorganism.

The colony count reduction in a given energy dosage may for example be at least 70%, or preferably at least about 90%. A 90% reduction can generally be effected by applying twice the $LD_{50}$ for a given target organism or an average of the $LD_{50}$'s for a spectrum of target organisms. The bacterial colony count can be determined by taking a biopsy of the target site using a suitable biopsy implement such for example as a scraper, swab or the like and cultivating the biopsied tissue through serial dilutions and determining the colony counts by known methods. Determinations of colony count reduction can be employed to calibrate the energy output of photothermal treatment instrument 10 to output one or more specific dosages determined to elicit a particular response in a patient or group or class of patients. Optionally photothermal treatment instrument 10 may have settable controls to provide different predetermined dosages, which controls may be labeled. For example, a duration controller may be provided for selecting the pulse duration or pulse width e.g. from about 10 to about 50 msec, and a pulse number selector may select the number of pulses output for a single actuation of photothermal treatment instrument 10, for example from 1-10 pulses, at a predetermined relaxation interval, for example of from about 10 to about 100 msec.

As described, the inventive treatments can be performed to obtain a desired temperature elevation of target tissue for a predetermined period of time or to obtain a desired microorganism colony count reduction. The treatments can also be performed to elevate the target tissue to a selected temperature or temperature range for a duration sufficient to obtain a desired colony count reduction in a target or sample microorganism or spectrum of microorganisms.

Chemical supplementation. If desired, various chemical means can be used to supplement the effect of the radiation or to sensitize the target microorganisms to the radiation, for example, stains or oxidants. Given the diversity and virulence of the colonies of organisms commonly responsibly for rhinitis and sinusitis, use of such a sensitizer is often desirable in the practice of the invention described herein. The treatment may, for example, be a photochemotherapeutic treatment, effected for example by employing an oxygen gel or other suitable material containing a biocompatible oxidant, e.g. hydrogen peroxide, in a concentration of from about 0.5 to about 5% by weight of the gel. The oxidant chemically sensitizes the bacteria or other microorganisms to the effects of the applied radiation.

Alternatively, the target organisms may be stained, e.g. with a food dye, a known bacterial stain, or other suitable stain which is adsorbed by or adheres to a target microorganism and enhances the absorption of light energy by the organism. Employing staining, desirably the stain color is selected to correspond with the applied light wavelengths, to enhance the effect, for example by using a blue or green stain with applied orange or red light and a red or orange stain with applied green or blue-green light.

Esthetic considerations can make staining problematic in the anterior oral cavity, especially in the vicinity of the teeth because the unsightly colored appearance of the tissues or teeth, induced by staining is likely to be visible to others during normal conversation and may linger for days. However, staining of the back of the tongue is less likely to be problematic and careful application of modest quantities of stain to the nasal and sinus cavities, pursuant to the present invention, is unlikely to be apparent to others. Accordingly, staining which enhances the lethal efficacy to microorganisms of applied radiation can be advantageous in the practice of the invention.

Such gels, stains or other topical target treatment compositions, for example local anesthetics, can advantageously be applied employing swabs, or other suitable means.

Target sites. The method and instruments of the invention, used separately or together, can be employed to treat a variety of target sites, including sino-nasal target sites, to control microorganisms infecting the target site. Exemplary target sites include either or both nostrils, the left or right lower nasal cavity, the left or right upper nasal cavity, the sinuses, especially those sinuses that are accessible via the nasal cavity and, if accessible, the frontal, ethmoidal, sphenoidal and maxillary sinuses. Various suitable instruments, including the instruments described herein, for treating one or more target sites, as well as other suitable target sites, will be apparent to those skilled in the art in light of the disclosure herein.

The sinuses are nominally air-filled bony cavities located in the face and skull adjacent to the nose. There are eight paranasal sinuses, which occur as "paired" structures. The right and left frontal sinuses are located in the forehead region; the maxillary sinuses are in the cheek area; the ethmoid sinuses are located between the eyes just behind the bridge of the nose; and the sphenoid sinuses lie deep in the center of the skull. Each sinus is connected to the nose by a small opening called an ostium, and has a size which may be as large as a walnut. The frontal sinuses are situated beneath the bone of the forehead and just in front of the bone overlying the brain.

The purpose or purposes of the sinuses is or are not yet fully understood and are variously described as being to lighten the skull, to improve vocal resonance and/or to produce liquid mucus that drains downwardly from the respective sinus cavity to the nasal cavity and throat and thence to the stomach. Pursuant to the latter theory the mucous fluid moistens the nasal cavity as it travels, preventing undue dryness inside of the nose and trapping and removing dust, dirt, pollutants and microbiologic organisms, preventing them from reaching and infecting or contaminating the lungs. Instead, in a healthy, functioning sino-mucal system such potentially harmful foreign matter is carried to the stomach and destroyed by gastrointestinal digestive factors.

In people with good upper respiratory tract health, tiny hair cells, called cilia, move the mucus layer toward the back of the nose and throat, where the material is ultimately swallowed. Mucus produced in the frontal sinus usually drains through the frontal recess, then through the ethmoid sinus, and ultimately into the nasal cavity. The size and nature of the connection between the frontal sinus and the nasal cavity is highly variable between individuals, making the performance of surgery to mitigate persistent chronic sinus conditions in this area a challenging task fraught with risk of damage to delicate anatomical structures.

Each ethmoid sinus comprises many chambers of 7 to 10 cells each, or smaller, that collectively make up the sinus. Ethmoid cells are composed of very thin-walled bone and lined with mucous membrane. Each cell has its own opening that ultimately leads into the nasal cavity. The ethmoid structure is highly variable and unique, like a fingerprint. The variability complicates the surgeon's task, as does the ethmoid sinuses' adjacency to the eyes and brain. The maxillary sinuses are two air-filled cavities within the maxilla, the bone that forms the cheek and upper jaw located above the teeth, below the eye, and just to the side of the nose. Each maxillary sinus is comprised of a single air-filled chamber lined with a mucus-producing membrane. The mucus travels from the maxillary sinus through an opening, or ostium, until it reaches the nose. Deep within the skull behind the ethmoid sinuses are the sphenoid sinuses, small cavities approximately the size of a large grape. The right and left sphenoid sit next to each other, separated by a thin "septum" or plate of bone. The sphenoid sinuses discharge mucus into the back part of the nose through an opening, or ostium in close proximity to the optical cortex and major vessels that carry blood to and from the brain. lie. Sinus disease, as well as surgery in the sphenoid area, carry special risks which may be mitigated by employing the methods and devices of the invention.

The relatively simple sinus applicators illustrated in FIGS. 3, 4 and 6 and alternative instruments, as will be apparent to those skilled in the art, are useful in many embodiments of the invention, as described hereinabove. however, more complex instruments may be employed, if desired. For example, a functional endoscope or microcatheter may be employed to access a desired target sinus site via the nasal cavity, and, if necessary via an ostium and may be operated, to apply a sensitizing agent followed by photic, laser or photothermal energy to the sinus site to destroy or debilitate infective microorganisms as described herein.

Dental regions of the anatomy are subject to special considerations regarding bacterial or other infections. Unique organisms may be implicated in the diseases of the teeth and the periodontal region and the distinctive nature of pathologies such as caries and gum disease, along with aesthetic and other considerations, render the treatment and prognosis of dental region infections to lie largely in the province of the profession of dentistry.

Target conditions. Target conditions that can be treated by the methods and instruments of the invention include low level or chronic infections of microorganisms comprising bacteria, fungi, viruses and any other microorganisms that may be present at the target site. The invention is particularly useful for treating persistent chronic rhinitis and sinusitis conditions that persist for extended periods, for example longer than four or six weeks. It will be understood that target conditions may comprise any or all of bacterial, fungal or viral population and that most target conditions will comprise a diversity of species although in some cases one or two or a small number of species may predominate. The invention is contemplated as being particularly useful for treating conditions that include species unresponsive to conventional treatments for example resistant bacteria, fungi and viruses. Target conditions to be treated by means of the invention may include one or more of any of the species of microorganism specifically named herein, and in particular those organisms named in the discussion of background art.

Thus, for example, nasal microbial populations including significant proportions of fungal and viral microbes can be treated with a photosensitizing blue or violet dye, e.g. gentian violet, and a suitable dosage of bright light from a photothermal or laser source e.g. a laser diode.

The inventive treatments are broad spectrum and are contemplated to be active or effective against each of the foregoing classes of microorganisms, namely bacteria, fungi and viruses. In particular the photothermal treatments of the invention are contemplated to be effective against antibiotic-resistant bacteria and anerobic bacteria. Furthermore, the treatments of the invention can be controlled to be effective against nonplaque bacteria and the invention includes treatments limited to control of nonplaque bacteria and other microorganisms. An ability of the invention to effectively treat antibiotic-resistant bacteria is especially advantageous. It is believed that the lethal modalities of photothermal energy bombardment and photic sensitization will be relatively unlikely to be overcome by adaptive organisms developing resistant strains.

Some of the conditions that can be treated by the nasally applied methods of the invention include stuffy or runny nose, viral infections such as colds of the upper respiratory tract, influenza, sinusitis, congestion and other low-level chronic infections of the nose and sinuses as well as more serious streptococcal or other bacterial or viral infections of the nose and sinuses. The invention is particularly, although not exclusively, useful for the treatment of infections having, or likely to have, bacterial, viral and fungal components, which may respond only poorly to other treatments.

Methods of Treatment. The microorganism control treatments and instruments of the invention are particularly suited for professional use, for example by doctors, dentists, suitably licensed medical practitioners or technicians or medical assistants, to treat patients in the practitioners' offices or other medical facility. However, the invention is not so limited and can be practiced in any suitable location, including hospitals and homes. Suitable treatment protocols may vary according to the severity and persistence of the infection, the responsiveness of an individual patient and the persistence of patient-perceived symptoms. Suitable treatment protocols can comprise diagnosis of a condition and its proximate cause, target site cleaning and preparation, application of a photochemical sensitizer or other useful agent, if desired and an individual procedure for application of photic or photothermal energy as described herein. With advantage, energy application can be performed on one or more infected target surfaces to a desired detectable conclusion, such as a tissue temperature elevation or microorganism colony count reduction.

The protocol may be repeated as infrequently as biweekly (every two weeks) or even monthly, or may be weekly or twice-weekly, depending upon the judgment of the physician. Also, the protocol may be continued indefinitely, e.g. for two or more years, or more desirably for no more than about one year.

In one preferred embodiment, treatments are performed approximately weekly or biweekly until symptoms are adequately relieved as determined by the treatment subject or their medical advisor. Other desirable embodiments of the invention comprise more frequent such procedures continued for shorter periods, for example from one to five times per week, desirably once or twice per week, for periods of from about two to about sixteen weeks preferably from about four to eight weeks for example for five or six weeks.

Individual treatment procedures can comprise one or two shots of energy applied for example to each nostril or to one or more target sinuses or to both the nostrils and one or more sinuses. Each individual procedure can have a duration of from about 10 seconds to about 10 minutes, preferably from about 30 seconds to about 2 minutes, per target site referring to the time that a treatment instrument is disposed to direct energy toward the target surface. The instrument may emit energy substantially throughout that time period or may emit one or more pulses of energy at intervals during the time period.

Preparatory steps of the energy treatment protocol can comprise verifying the patient's condition, for example as being a chronic rhinitis or sinusitis sufferer, and diagnosis of the character of the infection for example by sampling or taking a biopsy and employing microscope examination or other laboratory tests to determine the presence or concentration of one or more infectious species. The treatment protocol can, if appropriate be adapted according to the results of the diagnosis, for example to specifically target one or more organisms identified.

Usefully, nasal irrigation as known in the art, may be employed prior to the energy treatment if desired. For example with the head tilted forward to a point where the nasal passages are near horizontal, saline, isotonic or other suitable fluid can be flushed through the nose to remove mucous and detritus, employing a syringe or other suitable dispenser and a source of irrigation fluid. Optionally, the energy treatments described herein can be supplemented by subject-applied Nasal irrigations at suitable intervals, e.g. commencing at least twelve hours after an energy treatment, once or twice a day. A resiliently squeezable handheld bottle with a dispenser tube and nozzle, or other suitable self-applicator may be used for this purpose.

Such nasal irrigation or cleansing can be effected in a variety of ways employing a gravity flow, pressurized or other suitable device to apply a cleansing fluid to flush the nasal passages. The cleansing fluid may be clean water, or more desirably saline, isotonic or other suitable electrolyte-containing aqueous medium. Efficient nasal irrigation may assist with partial removal of mucous and other matter from the sinuses or sinus passageways. If desired, specialist techniques for clearing or cleansing the sinuses may be employed in the pretreatment some suitable ones of which are described hereinbelow.

A number of useful devices and procedures for cleansing or clearing the nasal passages that may be employed in the sino-nasal pretreatments of the invention are disclosed in "*Nuances of Nasal and Sinus Self-Help*" by Susan F. Rudy, Susan F. Rudy and Trafford Publishing (2004), in particular in Chapters 6, 7 and 8 at pages 61-89 relating to gravity-flow, low-pressure and electrically powered devices for nasal cleansing.

Some suitable gravity flow devices include: neti pots, in styles such as gravy boat, tea pot or rhino horn and which may be made of ceramic, metal, plastic; bags and douches. Some suitable low pressure devices include: aspiration devices; syringes and squeeze bottles in a variety of sizes; and pressurized sterile canisters of saline or other electrolyte solution. The latter may be advantageous in the clinic or medical office, enabling a single disposable product to be employed to nasally irrigate a patient or for a pretreatment, providing an efficient way of assuring each patient of a sterile treatment and avoiding cross-contamination from one patient to another.

Squeeze bottles suitable for nasal irrigation are available with capacities of from about 4 oz. to about 14 oz. from a number of suppliers including Kenwood Laboratories, Hydromed, Inc., Respironics, Inc., New York Sinus Center and others. Some bottles are prefilled with isotonic fluid. Some suppliers provide dry mixes that can be made up with water into suitable treatments fluids.

A wide range of electrically powered irrigators, including portable units, is available and may be employed in the nasal pretreatment procedures of the invention. Such irrigators apply irrigation fluid under pressure, optionally with pulsing, typically at a pressure in the range of about 5 to about 80 psi. In such devices, irrigation fluid may be electrically pumped from a bulk reservoir having a capacity of from about 80 ml to about 2 liters and is supplied via a short hose to a wand which has a suitable applicator tip which may be removable and optionally disposable. Different tips, wands or adapters may be provided to serve different purposes, for example, stream, spray, adjustable between the two, bulbous tip, straw-like tip, fanciful adapter tips for oral irrigators and so on. Some devices, provide for adjustable pressure, in various ranges from about 5 to about 100 psi. Other options include pulsing features providing a pulsed output in the range of from about 1,000 to 3,000 pulses per minute. Suppliers of such equipment include WaterPik Technologies, Hydro Med Inc. (Sherman Oaks, Calif.) Panasonic, Conair (Trumbull, Conn.), Sinus Pharmacy (Carpenteria, Calif.) and others.

In general, such nasal irrigation devices are used with the head tilted forward, and possibly also to one side, the with irrigation fluid being applied to one nostril and draining out of the other. Aspiration devices may draw congesting material from one nostril, while closing or partially closing the other, as necessary.

Usefully also, nasal cleansing can be practiced by the treatment subject, or patient on a routine basis, for example daily or twice daily between office visits for the primary, radiative treatments of the invention. It will be appreciated that the cleansing and clearing effected by such nasal cleansing treatments will usually be temporary. As mentioned, nasal cleansing may also effect some clearing of the sinuses or sinus passageways.

Desirable devices for professional use in a medical office, clinic or other treatment facility intended for multiple applications of irrigation fluid to a number of treatment patients or subjects desirably have means to control transmission of infectious agents from one patient to another. Removable and disposable applicator nozzles or other fittings can be useful in this respect. In addition, means to control possible runback of fluid from the patient are desirable. Such means may comprise a one-way valve to prevent runback being delivered to a subsequent patient. In one useful embodiment of such runback control means the one way valve is provided in a disposable applicator tip or adjacent conduit, which is also disposable. Optionally, the device can also include a manually operable shutoff valve just upstream of the point of connection of the disposable tip enabling the disposable tip to be easily removed and replaced, without loss of pressure, so that fluid discharge can be quickly resumed. Such shutoff valve may be manually operable and resiliently biased to a closed position or otherwise structured to close automatically. Other suitable structural measures for controlling runback will be apparent to those skilled in the art.

Nasal or sinus cleansing pretreatments such as described above can be helpful in enhancing the performance of the electromagnetic radiative treatments of the invention by improving the access of the radiation to deeper seated organisms that may be resident subepithelially or interstitially in cracks, crevices or folds of the tissues or other anatomical structures.

To perform a desired protocol on a patient to treat one of the described target conditions employing photothermal treatment instrument 10, the medical practitioner initially determines the desired energy output of the photothermal treatment instrument 10 by selecting an appropriate lamp 32 and filter or filters 34, 36. In addition, the practitioner sets controls for power output and duration of energy output to values selected to be appropriate for the target condition, if such controls are present or manually controls the instrument to output energy for a desired time period at a desired distance from the target.

The patient is prepped as necessary for example, by clearing or cleaning the nose or sinuses by more or less mechanical processes such as blowing or removal with a suitable implement. For some particularly useful embodiments of the invention, a sensitizer such as a dye is then applied, in liquid form using a swab or spray.

Some illustrative examples of sino-nasal treatment protocols according to the invention will now be described, by way of example, and without limitation.

EXAMPLE 1

Nasal Treatment Using Diode Laser Energy

In one example of a nasal treatment protocol, a patient attending a doctor's office presents symptoms of chronic sinusitis, complaining of a feeling of congestion, having nasal mucous an affected voice and headaches ranging from mild to severe. The following treatment protocol is performed.

1. The nose is cleaned of accumulated mucous and related detritus employing tissues and blowing or saline irrigation or both.
2. One or more endoscopic cultures is or are taken from the mucous membrane lining the affected area or areas of the nose, employing a small surgical scraper, to monitor what organisms are growing. This information is used to monitor the effectiveness of the treatment, and to adjust the dosage or frequency of treatment accordingly.
3. The affected nasal or sinus areas are coated with a concentration of about 0.5 mg/ml methylene blue, a blue-spectrum dye, employing an alginate swab (?check brochure).
4. A quiescent interval of from 1 to 20, preferably from about 5 to about 10 minutes prior to photothermal treatment is allowed for absorption of the applied stain.
5. The practitioner then applies a suitable dosage of radiation, employing diode laser energy applicator 110 fitted with nasal tip to provide a desired energy dosage to the internal surfaces of the nasal cavity. The energy applicator is carefully fitted to each nostril in turn and oriented to direct the output upwardly into the upper nasal cavity. An energy dosage of light at a wavelength of about 760 nm emanating from a laser diode at an energy of 50 milliwatts/cm2 for a duration of 30 seconds. is then output while the practitioner holds the applicator in position. Dosage is selected to reduce the heterogenous microbe population by about 50-90% leaving a residual colony to permit and encourage growth of normal microflora. A suitable dosage can be determined by in vitro testing, by culturing nasal samples before and after treatments or by both methods. Each diode laser energy treatment of a target nasal area is effected for from about 5 to about 15 minutes depending upon the judgment of the practitioner, for example for from about 10 to about 12 minutes, completing a nasal treatment of both sides of the nose in about 30-40 minutes.
6. Steps 1-5 are repeated every two weeks until symptoms abate. If appropriate, the treatment in step 5 is modified according to the results of the biopsy in step 2. For example??

EXAMPLE 2

Sinus Treatment Using Diode Laser Energy

The protocol of Example 1 is repeated employing a sinus applicator tip in place of the nasal tip. Each affected or targeted sinus is treated by inserting the sinus applicator tip through the nasal cavity and positioning the sinus applicator outlet as closely adjacent to the entrance to the respective sinus cavity as possible. A desired energy dosage is then output while the practitioner holds the applicator in position. of Such treatment can be effective in managing microbial blockage of the sinus drainage ducts bringing significant relief to some patients.

Similarly, each diode laser energy treatment of a target sinus volume is effected for from about 5 to about 15 minutes depending upon the judgment of the practitioner, for example for from about 10 to about 12 minutes, completing a treatment of the sinus passages on both sides of the nose in about 30-40 minutes.

The foregoing sinus treatment is preceded by, or alternatively, followed by, the nasal treatment of Example 1. The whole protocol, with application of radiation to all subject nasal and sinus target areas is completed within about 50-70 minutes.

EXAMPLE 3

Nasal and Sinus Treatments with Pulsed Photothermal Energy

The protocols of Examples 1 and 2 are repeated employing pulsed energy from a photothermal applicator equipped with a xenon flashlight having an orange filter, transmission about 600-700 nm. Two photothermal energy pulses of about 35 msec each, with a 50 msec interval, at an energy density of about 2.5 J/cm$^2$ are applied to each nostril and target sinus area. In this case with much shorter duration energy treatments, the whole protocol is completed in about 10-20 minutes, or possibly less.

EXAMPLE 4

Determination of Lethal Sensitization of Oral Pathogens

Suitable stain dosages for providing lethal sensitization of oral pathogens are determined in vitro by the following procedure. An objective is to determine the minimum duration of light exposure and minimum agent dilution required to achieve at least a 50% reduction in bacteria counts. Experimental tests are performed on two common pathogens using a continuously working, high intensity, red filtered halogen lamp. Red light from the filtered halogen lamp is transmitted through a flexible light guide to radiate downwardly onto petri dishes containing samples of live bacteria of species *Porphyromonas Gingivalis* and *Prevotella Intermedia* using the protocols described below.

Bacteria. *Prevotella Intermedia* is isolated from patient sample material, identified in the laboratory using standard diagnostic test systems (Remel Inc., Lenexa, Kans., USA) and is maintained by twice-weekly subculture in thioglycollate medium (Becton Dickinson and Co, Sparks, Md., USA). *P. gingivalis* ATCC 33277 obtained from Remel Inc., is maintained by a twice-weekly subculture on CDC anaerobe blood agar (Becton Dickinson and Co, USA) and in thioglycollate medium (Becton Dickinson and Co, USA).

Light Source. The source for light energy is a continuously working, high intensity halogen lamp having a built-in 250-Watt quartz halogen light source, model 1-250 supplied by Medithon, New York, N.Y., USA. Such lights are customarily employed for ear, nose or throat procedures. The light is transmitted through a flexible light guide and filtered to maintain maximum energy output at wavelengths in the vicinity of about 650 nm using a broadband red filter (Edmund Optics Inc., Barrington, N.J., USA). The light output power density measured at 3 cm distance from the end of the light guide with filter is about 50 milliwatts/cm2.

Photosensitizer. 1% methylene blue solution (Faulding Pharmaceutical Co, Paramus, N.J., USA) is used as a photosensitizer. Serial dilutions with water of initial solution with respective concentrations of 0.1%, 0.075%, 0.05%, 0.025% and 0.01% are prepared from the initial solution using sterile 10-ml bottles of normal saline and sterile syringes.

Lethal photosensitization of *P. Intermedia*. Petri dishes containing CDC anaerobe blood agar (Becton Dickinson and Co, USA) are inoculated with 0.5 ml of broth containing $5 \times 10^5$ CFU/ml and left closed at room temperature for about 10 minutes to let the broth penetrate the agar media. The inoculated plates are then exposed to 1 ml of methylene blue solution at concentrations 0.1%, 0.075%, 0.05%, 0.025% and 0.01% respectively for at least 60 seconds and then exposed to the red filtered light source for time intervals of 1 min, 5 min, 10 min and 20 min respectively. Only plates with concentrations of 0.01%, and 0.025% are used in the experiment with 20 min light exposure. Four plates are used for each experiment. Four inoculated plates that are not exposed to methylene blue or to the light source are used as controls. The controls are covered to protect them from ambient light. In order to examine the ability of light to cause killing of bacteria, inoculated plates are exposed to the red-filtered light at the same time intervals, without previous exposure to methylene blue, in the same groups of four plates. To study the ability of methylene blue alone to induce bacterial death, groups of four inoculated plates are exposed to the methylene blue solution at specified concentrations without subsequent exposure to the red-filtered high intensity light. A total of 108 subcultures is used for the experiment. Plates are incubated in anaerobic conditions in the jars using anaerobic pack kits (BBL GasPak Plus, Becton Dickinson and Co, Sparks, Md., USA) at 37° C. for 24 hours. Samples of the resulting culture growth are taken from each plate with sterile 1:L standard loop, dispensed in 1 ml of sterile NS and placed at the same media. Cultures are incubated at anaerobic conditions at 37° C. for another 24 hours, and after that the resulting colony count is performed on each plate.

Lethal photosensitization of *P. Gingivalis*. Serial dilutions of the *P. gingivalis* culture are prepared from the initial culture preserved on plates using 1:L sterile standard loop (Becton Dickinson and Co, USA) and sterile NS. AVitek calorimeter (Hach Company, Loveland, Colo., USA) is used to achieve a final concentration of about $5 \times 10^3$ CFU/ml from an initial 0.5 standard McFarland suspension of 108 CFU/ml. Plates containing CDC anaerobic blood agar (Becton Dickinson and Co, USA) are inoculated with the resulting suspension using sterile 10:L standard loops (Becton Dickinson and Co, USA). The plates are then exposed to the methylene blue solution at different concentrations and thereafter to the red-filtered high-intensity light source at different time intervals using the algorithm described for *P. Intermedia*. Plates are also incubated at 37° C. in the tightly closed jars supplied with anaerobic pack kits (BBL GasPak Plus, Becton Dickinson and Co, USA) for 24 hours, and the resulting colony count is performed on each plate.

Typical results obtainable from experiments such as those described in Example 2 are shown in Table 1 below, which describes the data as the means of four values, two each from each species, along with their standard deviations. The results for the two species were broadly comparable. Statistical analyses can be carried out using single-factor analysis of variance.

TABLE 1

Survival of Bacteria Exposed to Blue Stain and Red light
Percent of living bacteria

| Methylene blue % | Exposure to Red Light | | | | |
|---|---|---|---|---|---|
| | 0 | 1 min | 5 min | 10 min | 20 min |
| 0 | N/A | 70 +/− 6 | 75 +/− 7 | 73 +/− 8 | N/A |
| 0.01% | 70 +/− 11 | 73 +/− 6 | 69 +/− 7 | 55 +/− 6 | 51 +/− 4 |
| 0.025% | 75 +/− 14 | 67 +/− 4 | 47 +/− 6 | 48 +/− 8 | 49 +/− 5 |
| 0.05% | 68 +/− 12 | 53 +/− 10 | 32 +/− 7 | 32 +/− 9 | N/A |
| 0.075% | 51 +/− 10 | 45 +/− 5 | 26 +/− 5 | 25 +/− 5 | N/A |
| 0.1% | 35 +/− 9 | 39 +/− 12 | 28 +/− 9 | 24 +/− 4 | N/A |

Column 1 of Table 1 reports the concentration of stain employed in each culture as a percent of methylene blue, "methylene blue %". The remaining column headings describe the duration of red light exposure in each test.

Results. It may be seen from the data in Table 1 that a statistically significant reduction in bacterial colony count, with a survival rate of 50% or less can be achieved at concentrations of methylene blue of 0.05% and higher when the red light exposure is 10 or 20 minutes. No statistically significant difference is noted between the exposure for 10 and 20 minutes in either species or with any concentration of methylene blue. Exposure of both cultures to red-filtered high-intensity light source may produce statistically significant increased killing with duration as read at the time intervals of 1 min, 5 min and 10 min, with methylene blue concentration of 0.05%, and at the time intervals of 5 and 10 min with methylene blue concentration of 0.025%. Methylene blue concentrations of 0.075% and 0.1% show significant bactericidal effect even without light exposure. Some statistically significant bacterial killing can also be at a 0.01% concentration without light exposure in the *P. gingivalis* culture. With light exposure for 1 min both 0.075% and 0.1% concentrations of methylene blue produced statistically significant bacterial count reduction in both cultures. Little, if any statistically significant reduction in bacterial counts is noted with the exposure of either culture to the red-filtered high-intensity light source without the exposure to methylene blue.

Conclusion. The results of the study show that red-filtered high-intensity light, used in combination with methylene blue solution at a concentration of 0.01% or higher, can produce a bactericidal effect on both species examined, when a time of exposure less than 10 minutes and an accumulated energy level of 30 J/cm$^2$ are employed. Significant reduction in bacteria counts can also be achieved with combination of light exposure for 5 min and methylene blue concentration of 0.025% and light exposure for 1 min and methylene blue concentration of 0.05% and higher. Methylene blue can produce bactericidal effect on *P. gingivalis* at concentration of 0.1%. Exposure to red light with wavelength of 650 nm alone does not appear to produce significant killing of *P. intermedia* or *P. gingivalis*.

Furthermore, as may be seen from the data in Table 1 that a desired level of lethal photosensitization, namely killing of 50% or more of the bacteria population, of the studied oral pathogens can be achieved under the following conditions:

1. Illumination with red halogen light for 5 minutes or more using 0.05% methylene blue stain; or
2. Exposure to red halogen light for 20 minutes in the presence of a concentration of 0.025% or 0.01% methylene blue stain.

It may be understood that some useful conditions to avoid tissue damage and destruction of commensal organisms, while obtaining useful kill rates of target bacteria are, for example, 8-12 min at 0.01%, 4-6 min at 0.025% and equivalent combinations of concentration and exposure.

The useful conditions that are apparent from Table 1 and the accompanying discussion can be understood to be exemplary of a range of possible effective conditions that may be apparent, or may be determined with modest experimentation, and which may vary according to the particular stain employed, the prevalent species of microorganism and the wavelength and energy density of the applied light. For example, it is contemplated that use of a pulsed xenon photothermal light source as described herein can significantly reduce the exposure periods required for desired lethality.

Neither exposure to the halogen light for 20 minutes in the absence of a photosensitizer, in this case methylene blue, nor concentrations of methylene blue of 0.001% or 0.025%, without halogen light, appeared to be effective in killing bacteria.

Reduction of bacteria treated with 0.05% methylene blue alone, without exposure to light, is found to be insignificant. However, concentrations of 0.075% and 0.1% methylene blue are found to be significantly bactericidal, for the test species, even in the absence of red halogen light.

The data shows that lethal photosensitization of two common oral pathogens can be obtained employing high intensity red-filtered halogen light in the presence of dilute methylene blue verifying the value of chemical photosensitization and suitable applied light as a treatment alternative to chemical antibiotics which may induce resistance. Though not demonstrated by the tests described here, unlike chemical antibiotics, combinations of halogen light and suitable stains may also destroy non-bacterial organisms such as fungi and viruses.

In a still further embodiment, the invention provides methods and apparatus wherein the bacterial populations at the target are quantitatively monitored by species or strain on a relative or absolute basis. The treatment protocol or dosage can then be varied according to the data obtained regarding the increase or decrease of one or more bacterial populations with time. Thus, for example, treatment may be continued until a desired low level of one or more undesired or pathological bacteria is reached. In one embodiment of the invention treatment is conducted to eliminate most but not all micro-organisms, for example to destroy or kill from about 50 to about 90 percent of a target species or heterogenous population of species, so as to permit desirable organisms, associated with health to survive. Possibly, treatment may be continued until a desired increase in level of a bacterium associated with health is reached.

If desired the treatment apparatus can include a power unit having user-settable controls to provide a desired photothermal output enabling the operator to select a desired pulse energy, pulse duration, number of pulses and so on, preferably, using an electronic display to give a visual indication of the settings. Also, the power unit may provide a number of treatment selections each representing a particular combination of pre-set output characteristics suitable for a particular purpose, for example, for treating a specific bacterial strain, a specific patient condition or other suitable parameters. The programming of same can be managed by a microprocessor and suitable software if desired included in or operatively connected with the power unit.

While the invention has been described in the context of a handpiece intended for manipulation by a human user, the invention also includes robotic or remote operation of any of the devices described herein or modifications thereof designed for remote or robotic operation with either manual simulations or electronic actuation of the operator movements that would otherwise be required to conduct the procedure.

Many embodiments of the invention are suitable for, and the invention includes, the practice or use in a doctor's or dentist's office, or clinic of, photothermal and other treatments with photic or thermal energy of halitosis, and other oral or other bodily cavity infections with bacteria or other microorganisms on an out-patient or other basis. Self-administration and home use applications by a parent, nurse, caregiver or the like of embodiments of the invention will also be apparent to those skilled in the art and are embraced by the invention.

Consumer Product. The products and processes of the invention are suitable for use by consumers either for self-application or for one person to apply to another. If desired, particularly, although not exclusively, for consumer use, photothermal treatment instrument 10 can have a limited energy output intended to prevent user injury or abuse which may limit the maximum pulse intensity and/or the number of pulses that can be emitted in a given time period. For example the instrument may have a delay which prevents further operation for a period of from about 10 to about 30 minutes after a given number of pulses has been generated, for example from about 5 to about 10 pulses. Such a feature may prevent consumers or others overdosing and causing tissue damage.

Possible mechanism of action. While the invention is not limited by any particular theory, it will be understood by those skilled in the art that heat acts destructively on microorganisms by raising the temperature of their immediate environment. In contrast, a probable mechanism for the bactericidal properties of light is that of catalytic liberation of highly reactive species such as superoxides and free radicals which destroy sensitive molecules for example DNA in the bacteria.

If desired the photoactivated energy treatments described herein, optionally employing photosensitizers such as stains, can be employed as an adjunct to or alternative to nasal or sinus surgery.

The invention furthermore includes rhinosinusitis treatment methods and apparatus for practicing same employing a herein described inventive light-utilizing therapy augmented by a conventional rhinitis or sinusitis treatment. Such conventional rhinosinusitis treatments include not only the nasal irrigation therapies described herein but also, as alternatives or adjuncts to such irrigation therapies, application of one or more chemically or pharmaceutically active agents such as an anti-infective, anti-inflammatory or mucolytic agent as is known or becomes known in the art.

The active agent may be administered in any suitable manner, for example by spray, drops or vapors, as an aerosol, or optionally with the assistance of a nebulizer. If desired, the active agent may be administered in solution, optionally as a unit dosage, employing a surfactant. Also, if desired, the droplet or particle size may be controlled or selected for efficacy, for example as described in Osbakken et al. (supra). Any of the known or novel sinusitis treatments and apparatus, including the illustrated nebulizer, disclosed or referenced by Osbakken et al. may be employed as such adjunctive treatments to the light-utilizing therapies described herein. Such adjunctive treatment may be effected at any appropriate time in relation to the light-utilizing therapy, for example immediately prior thereto, from 1 to 6 hours prior thereto and/or on an ongoing daily, twice daily or more frequent basis between light-based treatments.

Though described in relation to the treatment of nasal and nasally accessed sinus cavities, it will be understood that the principles of the invention can be applied to the treatment of target sites, and especially mucous tissues, in other externally accessible bodily cavities.

Treatment of nonhuman mammals. While the invention has been described in relation to the control of microorganisms in nondental cavities of the upper respiratory tract in humans, it will be understood that the principles of the invention can also be applied to non-human mammals including for example, horses, cattle, sheep and other husbanded animals, pets such as dogs and cats, laboratory animals for example mice, rats and primates, animals employed for sports, entertainment, law enforcement, draft usage, zoological or other purposes.

Disclosures Incorporated. The entire disclosure of each and every United States patent and patent application is hereby incorporated by reference herein.

While illustrative embodiments of the invention have been described above, it is, of course, understood that many and various modifications will be apparent to those of ordinary skill in the relevant art, or may become apparent as the art develops. Such modifications are contemplated as being within the spirit and scope of the invention or inventions disclosed in this specification.

The invention claimed is:

1. A method of controlling microorganisms in the sino-nasal tract of a subject, the method comprising:
taking a culture from a microorganism-infected mucosal surfaced target site in the sino-nasal tract of the subject,
selecting a treatment dosage based on information provided by the culture,
applying visible spectrum electromagnetic energy to the microorganism-infected mucosal surfaced target site in the sino-nasal tract in the treatment dosage, the treatment dosage being effective to control the microorganisms without physiological damage to the subject,
applying a stain to the target site to sensitize the microorganisms to the visible spectrum electromagnetic energy prior to applying the visible spectrum electromagnetic energy, and
applying, as an adjunctive treatment, at least one chemically or pharmaceutically active agent.

2. A method according to claim 1 comprising employing electromagnetic energy having an energy peak overlapping with an absorption peak of the stain, the method optionally employing orange or red light respectively with a blue or green stain respectively.

3. A method according to claim 1 wherein the target site is a sinus and the method comprises inserting an electromagnetic energy applicator output port through a nostril, positioning the electromagnetic energy applicator output to address the target sinus site and outputting the electromagnetic energy from the output port in a direction transverse to the direction of insertion of the output port through the nostril optionally by supporting the light output port on a light transmitting neck having a curvature enabling the light output port to be oriented to output light to the target site in a direction transverse to the direction of insertion through the nostril.

4. A method according to claim 1 wherein the electromagnetic energy is applied with an energy density at the target site of from about 0.5 to about 3 Joule/cm$^2$.

5. A method according to claim 1 wherein the electromagnetic energy has an energy density at the target site of from about 0.5 to about 3 Joule/cm$^2$ and wherein the energy application, has a duration of from about 20 seconds to about 2 minutes, is performed at a frequency of from about one to about twenty times per month, optionally from about two to about ten times per month, for a period of from about two weeks to about six months.

6. A method according to claim 1 comprising controlling the energy application to comprise sufficient photothermal energy to effect, in a single treatment, a microorganism count reduction of at least about 80 percent.

7. A method according to claim 1 wherein the energy application is effected to raise the temperature of the target tissue to a temperature in the range of from about 50° C. to about 70° C.

8. A method according to claim 1 wherein the microorganisms comprise a heterogenous bacterial population including anaerobic bacteria, a fungal population, a viral population, or a mixed population, the mixed population comprising bacteria and fungus or bacteria and virus or comprising bacteria and fungus and virus.

9. A method according to claim 1 wherein the stain is selected from the group consisting of methylene blue, arianor steel blue, toluidine blue, tryptan blue, crystal violet, azure blue cert, azure B chloride, azure 2, azure A chloride, azure B tetrafluoroborate, thionin, azure A eosinate, azure B eosinate, azure mix sicc., azure II eosinate, haematoporphyrin HCl, haematoporphyrin ester, aluminum disulfonated phthalocyanine, and mixtures of the foregoing stains.

10. A method according to claim 1 wherein the at least one active agent is administered in solution, optionally as a unit dosage, the solution employing a surfactant and being administered as droplets or particles.

11. A method according to claim 1 wherein the microorganisms in the sino-nasal tract further comprise fungal or viral microorganisms or both fungal and viral microorganisms.

12. A method according to claim 1 performed to leave a residual population of at least 10 percent of the initial microorganism population.

13. A method according to claim 1 wherein the duration and energy density of the application of the visible spectrum electromagnetic energy are controlled to heat the stained microorganisms to a destruction temperature in the range of from about 50° C. to about 70° C. and to avoid physiological damage.

14. A method according to claim 1 comprising passing an electromagnetic energy applicator output through a nostril of the subject and applying visible electromagnetic energy with an intensity of from about 0.5 to about 3.0 J/cm$^2$ at the target site.

15. A method according to claim 1 comprising passing an electromagnetic energy applicator output through a nostril of the subject, and applying visible electromagnetic energy from a laser source to the target site with an intensity of from about 0.5 to about 3.0 J/cm² at the target site wherein the visible electromagnetic energy is passed through a diffuser to spread the laser beam for application to the target site.

16. A method according to claim 1 comprising employing a handheld energy applicator instrument having an energy output port receivable in a nostril of the treatment subject and inserting the applicator energy port into a nostril of the subject prior to the application of photothermal energy, the handheld energy applicator instrument comprising a handholdable body, a light output head bearing the light energy output port and a sinus treatment extension extending from the handholdable body wherein the sinus treatment extension comprises an extended and curved light transmitting neck supporting the light output port to permit the light output port to be passed through a nostril of the treatment subject and to be positioned to address a selected sinus area, the method comprising passing the light output port through a nostril of the treatment subject to be positioned to address a selected sinus area and applying the visible spectrum electromagnetic energy through the light output port to the selected sinus area wherein curvature in the curved light transmitting neck orients the light output port to direct light output from the light output port transversely of the sinus extension.

17. A method according to claim 1 wherein the at least one active agent is an anti-infective agent, an anti-inflammatory agent or a mucolytic agent.

18. A method according to claim 1 comprising administering the at least one active agent by a mode of administration selected from the group consisting of topically, as a spray, as drops, as droplets, as a vapor, as an aerosol, and with the assistance of a nebulizer.

19. A method according to claim 1 wherein the target site is infected with at least one species of microorganism selected from the group consisting of *Staphylococcus aureus, alpha-hemolytic streptococci, Streptococcus pneumoniae, Haemophilus influenzae* and coagulase-negative *Staphylococci*.

20. A method of controlling microorganisms in the sino-nasal tract of a subject, the method comprising applying visible spectrum electromagnetic energy together with longer wavelength energy to a microorganism-infected target site in the sino-nasal tract in a dosage effective to control the microorganisms without physiological damage to the subject, wherein the longer wavelength energy comprises RF energy in a wavelength range of from about 300 kHz to about 100 MHz optionally with an output power of from about 5 W to about 200 W and wherein the RF energy is pulsed with a pulse duration from about 1 msec to about 500 msec and a pulse rate of from about 0.1 pulses per second to about 10 pulses per second.

21. A method according to claim 1 comprising applying longer wavelength energy together with the visible spectrum electromagnetic energy to the microorganism-infected target site wherein the longer wavelength energy comprises microwave energy and wherein the microwave energy comprises a frequency or frequencies in the range of from about 100 MHz to about 50,000 MHz.

\* \* \* \* \*